(12) United States Patent
Cowles et al.

(10) Patent No.: US 10,787,697 B2
(45) Date of Patent: Sep. 29, 2020

(54) QUANTIFICATION OF NUCLEOSOME MODIFICATIONS USING CHEMICALLY-DEFINED RECOMBINANT NUCLEOSOMES

(71) Applicant: EPICYPHER, INC., Durham, NC (US)

(72) Inventors: Martis William Cowles, Chapel Hill, NC (US); Matthew F. Whelihan, Durham, NC (US); Andrea L. Johnstone, Apex, NC (US); Michael-Christopher Koegh, Cambridge, MA (US); Zu-Wen Sun, Brentwood, TN (US); Nathan W. Hall, Chapel Hill, NC (US); Matthew R. Marunde, Carrboro, NC (US)

(73) Assignee: EpiCypher, Inc., Durham, NC (US)

( * ) Notice: Subject to any disclaimer, the term of this patent is extended or adjusted under 35 U.S.C. 154(b) by 0 days.

(21) Appl. No.: 16/678,686

(22) Filed: Nov. 8, 2019

(65) Prior Publication Data

US 2020/0071745 A1    Mar. 5, 2020

Related U.S. Application Data

(63) Continuation of application No. PCT/US2019/020283, filed on Mar. 1, 2019.

(60) Provisional application No. 62/637,066, filed on Mar. 1, 2018.

(51) Int. Cl.
| | |
|---|---|
| *C12Q 1/6804* | (2018.01) |
| *C12Q 1/6811* | (2018.01) |
| *G01N 33/49* | (2006.01) |

(52) U.S. Cl.
CPC .......... *C12Q 1/6804* (2013.01); *C12Q 1/6811* (2013.01); *G01N 33/49* (2013.01); *C12Y 301/31001* (2013.01)

(58) Field of Classification Search
None
See application file for complete search history.

(56) References Cited

U.S. PATENT DOCUMENTS

| | | |
|---|---|---|
| 9,128,086 B2 | 9/2015 | Bawden et al. |
| 1,008,748 A1 | 10/2018 | Muir et al. |
| 2007/0160989 A1 | 7/2007 | Bawden et al. |
| 2013/0217027 A1 | 8/2013 | Bernstein et al. |
| 2014/0206014 A1 | 7/2014 | Micallef |
| 2014/0363812 A1* | 12/2014 | Micalef ............... C12Q 1/6804 435/6.11 |
| 2016/0341743 A1 | 11/2016 | Ruthenburg et al. |
| 2019/0064184 A1* | 2/2019 | Eccleston ........ G01N 33/57488 |

FOREIGN PATENT DOCUMENTS

| | | |
|---|---|---|
| WO | 2014/131841 | 9/2014 |
| WO | 2015/104431 | 7/2015 |

OTHER PUBLICATIONS

Thalin et al. (Innnnunol. Res. 2017 65:706-712) (Year: 2017).*
International Search Report and Written Opinion corresponding to International Application No. PCT/US2019/020283 dated Jun. 14, 2019.
Licht et al. "Plasma Levels of Nucleosomes and Nucleosome-Autoantibody Complexes in Murine Lupus", Arthritis & Rheumatism 44(6):1320-1330 (2001).
Eccleston, 13th Annual Biomarkers Congress, Manchester, UK, Feb. 15-16, 2018.

* cited by examiner

*Primary Examiner* — Changhwa J Cheu
(74) *Attorney, Agent, or Firm* — Myers Bigel, P.A.

(57) ABSTRACT

The invention relates to the use of recombinant/semi-synthetic nucleosomes carrying histone and/or DNA modifications as a reference standard for quantification of covalently modified (on the histone proteins or wrapping DNA), variant, or mutant nucleosomes (collectively "modified nucleosomes" or "nucleosome modifications") from a biological sample. The invention further relates to methods of using the assay to accurately quantify single or combinatorial nucleosome modifications as biomarkers of disease.

27 Claims, 5 Drawing Sheets

FIGS. 3A-3C
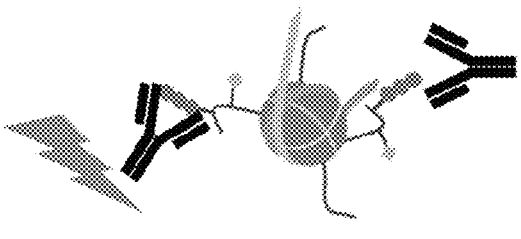
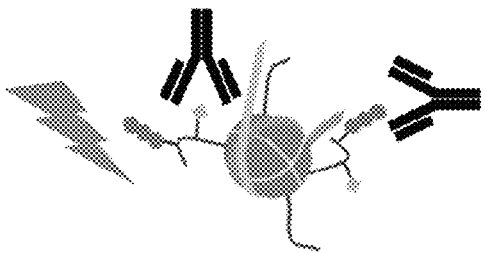
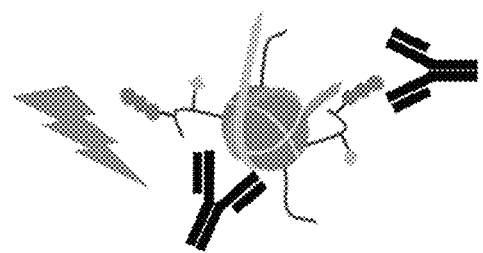
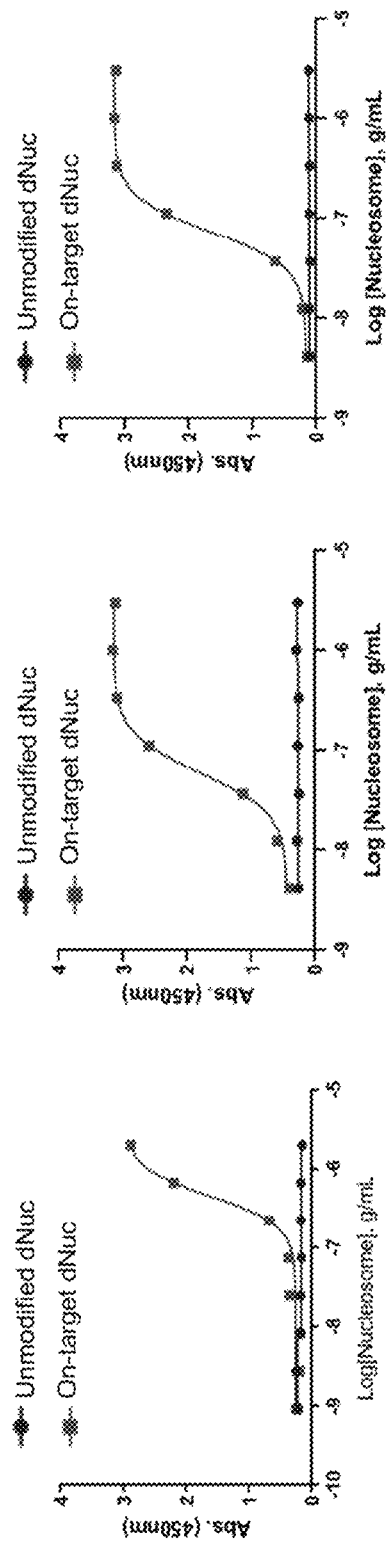

QUANTIFICATION OF NUCLEOSOME MODIFICATIONS USING CHEMICALLY-DEFINED RECOMBINANT NUCLEOSOMES

STATEMENT OF PRIORITY

This application is a continuation of and claims priority to International Patent Application No. PCT/US2019/020283, filed Mar. 1, 2019, which claims the benefit of U.S. Provisional Application Ser. No. 62/637,066, filed Mar. 1, 2018, the entire contents of each of which are incorporated by reference herein.

FIELD OF INVENTION

The invention relates to the use of recombinant/semi-synthetic nucleosomes carrying histone and/or DNA modifications as a reference standard for quantification of covalently modified (on the histone proteins or wrapping DNA), variant, or mutant nucleosomes (collectively "modified nucleosomes" or "nucleosome modifications") from a biological sample. The invention further relates to methods of using the assay to accurately quantify single or combinatorial nucleosome modifications as biomarkers of disease.

BACKGROUND OF INVENTION

Nucleosomes are the repeating units of chromatin, consisting of 147 base pairs of DNA integrally wrapped around a histone octamer (containing 2 copies each of the core histones (H2A, H2B, H3 and H4)) (Margueron et al., *Nat. Rev. Genet.* 11(4):285 (2010)). Changes in chromatin structure and function regulate diverse cellular activities including gene expression, DNA repair, chromosome transmission, and cell differentiation (Brown et al., *Hum. Mol. Genet.* 21(R1):R90 (2012); Lahtz et al., *J. Mol. Cell. Biol.* 3(1):51 (2011); Lunyak et al., *Hum. Mol. Genet.* 17(R1):R28 (2008); Reik, *Nature* 447(7143):425 (2007)). These processes are mediated in part by reversible histone post-translational modifications (PTMs; e.g., lysine methylation or acetylation), which have direct effects or are 'read' by effector binding proteins to transduce specific downstream signaling pathways. To date, over 100 unique histone PTMs have been identified, many of which are linked to human diseases, ranging from neurodegeneration (Landgrave-Gomez et al., *Front. Cell. Neurosci.* 9:58 (2015)) and metabolic syndrome (DelCurto et al., *Curr. Opin. Clin. Nutr. Metab. Care* 16(4):385 (2013); Wang et al., *Antioxid. Redox Signal* 17(2):282 (2012)) to cancer (Chopra et al., *Cancer Genet.* 208(5):192 (2015); Greenblatt et al., *Leukemia* 28(7):1396 (2014); Gajer et al., *Oncogenesis* 4:e137 (2015); Witt et al., *Curr. Pharm. Des.* 15(4):436 (2009); Hanmod et al., *Pediatr. Blood Cancer* 62(1):52 (2015); Kobayashi et al., *Oncogene* 32(21):2640 (2013)). Significantly, PTM-interacting proteins (aka 'readers') are highly druggable making them exceptional therapeutic targets for myriad human diseases/disorders (Arrowsmith et al., *Nat. Rev. Drug Discov.* 11(5):384 (2012)). Moreover, histone PTMs are an emerging class of cancer biomarkers that may be useful for early disease detection and prognosis as well as informing personalized treatment strategies (Khan et al., *World J. Biol. Chem.* 6(4):333 (2015); Chervona et al., *Am. J. Cancer Res.* 2(5):589 (2012)).

The cooperative function between histone PTMs and chromatin regulatory proteins represents a complex, systems-level signaling network, and its effective interrogation requires nucleosome-based tools. Multivalency (i.e., multiple reader domains within a given protein) is a common feature of chromatin regulators (Ruthenburg et al., *Nat. Rev. Mol. Cell. Biol.* 8(12):983 (2007)), and thought to serve as a key means by which histone interactions are regulated in a context-specific manner. Indeed, reader binding (and subsequent changes in cellular regulation) is vastly altered in the presence of various PTMs or combinations thereof, a hypothesis known as the histone code (Strahl et al., *Nature* 403(6765):45 (2000); Jenuwein et al., *Science* 293(5532):1074 (2001)). For example, the bromodomain PHD finger transcription factor (BPTF) reader protein contains domains with low individual binding affinity for H3K4me3 ($K_d$=~1 µM) and H4K12ac ($K_d$=~60 µM) (Li et al., *Nature* 442 (7098):91 (2006)), but this is significantly increased (>3-fold vs. H3K4me3 alone) in the presence of H3K4me3/H4K12ac combinatorially modified mononucleosomes (Ruthenburg et al., *Cell* 145(5):692 (2011)). BPTF is an anti-cancer therapy target (Dar et al., *J. Natl. Cancer Inst.* 107(5) (2015)); with high levels also found in amyotrophic lateral sclerosis patients (Mu et al., *Exp. Neurol.* 146(1):17 (1997)). Interestingly, H3K4me3 and H3/H4 acetylation co-exist at active promoters (Zhang et al., *EMBO Rep.* 16(11):1467 (2015)), and H3K4me3 has been shown to promote histone acetylation through effector recruitment (Tang et al., *Cell* 154(2):297 (2013)). Mechanistic studies have only begun to unravel the combinatorial impact of histone PTMs on cellular physiology, a necessary precursor to investigating the diseased state. As an example, changes in the gut microbiome (caused by diet) can have a significant impact on specific combinations of histone PTMs in host tissue (Krautkramer et al., *Mol. Cell* 64(5):982 (2016)). In a similar vein, recent findings suggest that combinatorial nucleosomal PTMs (vs. single PTMs) may provide better prognostic biomarkers of lung cancer (Shema et al., *Science* 352(6286):717 (2016)).

Effective presentation of combinatorial histone PTMs depends on the three-dimensional structure of the intact nucleosome, which serves as the scaffold for physiological PTM-protein interactions. Understanding the nature of the histone combinatorial code is vital if we are to translate the connection between epigenetic regulation and disease into next generation therapeutics and biomarkers. This is particularly true for histone methylation and acetylation, which play integral roles in chromatin regulation and disease (Greer et al., *Nat. Rev. Genet.* 13(5):343 (2012); Filippakopoulos et al., *Nat. Rev. Drug Discov.* 13(5):337 (2014); Soshnev et al., *Mol. Cell* 62(5):681 (2016)).

Several methods have been developed for the quantification of histone PTMs from biological samples (Sidoli et al., *J. Vis. Exp.* 2016 (111); Onder et al., *Expert Rev. Proteomics* 12(5):499 (2015); Machleidt et al., *J. Biomol. Screen.* 16(10):1236 (2011)), most of which rely on the use of modification specific antibodies for nucleosome enrichment (e.g., Chromatin ImmunoPrecipitation; ChIP) or detection (e.g., ELISA or Alpha). ELISA is commonly used to quantify histone or DNA modification from biological samples, with specific assays developed to directly quantify modifications on histones or nucleosomes using various antibody capture approaches. Nucleosome-based detection is superior to histone-based for two reasons:

1) nucleosome-based methods do not require acid-extraction steps, which are laborious and introduce variability; and,
2) nucleosome-based assays allow quantification of combinatorial modifications in trans (e.g., histone-histone, DNA-DNA, or histone-DNA combinations), impossible to monitor using histone subunits or DNA alone.

Despite these major advantages, current nucleosome-based assays lack proper controls for quantification. Indeed, assays using the current art are qualitative, with PTM levels reported as relative measurements or normalized using exogenous xenochromatin (e.g., avian, yeast or insect). The use of purified exogenous chromatin preparations can introduce a range of problems, as these reagents are poorly defined (at the PTM-specific level) and show batch variability, limiting their use for assay normalization (across experiments or even laboratories). Over and above this, it is currently challenging to determine if combinatorial marks are truly presented on the same nucleosome rather than coincident in the total pool.

Given the above, there is a need in the art for improved controls for nucleosome-based assays that detect histone and/or DNA modifications from biological samples.

SUMMARY OF INVENTION

The present invention relates to the use of recombinant/semi-synthetic/designer nucleosomes (hereafter referred to as "recombinant nucleosomes") carrying histone and/DNA modifications as quantification standards for calibration. Unlike the purified chromatin extracts in current use, the present assay utilizes fully defined recombinant/semi-synthetic nucleosomes for accurate quantification of single or combinatorial nucleosomal modifications. Similar to standards commonly used in the art, modified nucleosomes will be assayed in the same experiment (treated identically to samples) to generate a standard curve for assay quantification. Quantification of single or combinatorial nucleosome PTMs may provide better biomarkers for disease than the relative measurements in current use.

Significantly, the inventors have determined that only nucleosomes provide useful reference standards in plasma samples. When histones or nucleosomes are added to plasma, only the latter are recovered at predicted values, and thus viable for quantification. In this manner, the nucleosomes of the present invention provide useful standards for assays that quantify circulating nucleosomes directly from plasma or other bodily fluids.

Thus, one aspect of the present invention relates to a method for quantifying the abundance of a nucleosome modification (histone or DNA) in a biological sample, the method comprising:
 a. isolating a biological sample;
 b. preparing a library of native mono- and/or polynucleosomes from the biological sample, wherein the library comprises nucleosomes comprising one or more core histone and/or DNA modifications in a target epitope;
 c. preparing a recombinant mono- and/or polynucleosome sample comprising a core histone and/or DNA modification target epitope;
 d. providing the recombinant nucleosome sample at various concentrations to create a reference standard;
 e. adding an affinity reagent to the native nucleosome library and recombinant nucleosome references;
 f. performing an affinity reagent-based assay to measure the amount of nucleosome modification in the native nucleosome library and the recombinant nucleosome reference standard; and
 g. quantifying the abundance of nucleosome modification in the target epitope by comparing the relative abundance in the native nucleosome library to the reference standard.

Another aspect of the present invention relates to a method for quantifying the abundance of two or more modifications (histone or DNA) on a single nucleosome in a biological sample, the method comprising:
 a. isolating a biological sample;
 b. preparing a library of native mono- and/or polynucleosomes from the biological sample, wherein the library comprises nucleosomes comprising two or more core histone and/or DNA modifications in target epitopes;
 c. preparing a recombinant mono- and/or polynucleosome sample comprising nucleosomes carrying the two or more histone and/or DNA modification target epitopes;
 d. providing the recombinant nucleosome sample at various concentrations to create a reference standard;
 e. adding two or more affinity reagents to the native nucleosome library and recombinant nucleosome references;
 f. performing an affinity reagent-based assay to measure the amount of nucleosome modification in the native nucleosome library and recombinant nucleosome reference standard; and
 g. quantifying the abundance of nucleosome modification in the target epitopes by comparing the relative abundance in the native nucleosome library to the reference standard.

A further aspect of the present invention relates to a method for quantifying the abundance of one or more nucleosome modifications (histone or DNA) in a biological sample from a subject having a disease or disorder, the method comprising:
 a. isolating a biological sample from the subject;
 b. preparing a library of native mono- and/or polynucleosomes from the biological sample, wherein the library comprises nucleosomes comprising one or more core histone and/or DNA modifications in a target epitope(s);
 c. preparing a recombinant mono- and/or polynucleosome sample comprising nucleosomes carrying the one or more histone and/or DNA modification target epitopes;
 d. providing the recombinant nucleosome sample at various concentrations to create a reference standard;
 e. adding one or more affinity reagents to the native nucleosome library and recombinant nucleosome references;
 f. performing an affinity reagent-based assay to measure the amount of nucleosome modification in the native nucleosome library and recombinant nucleosome reference standard; and
 g. quantifying the abundance of nucleosome modification in the target epitope by comparing the relative abundance in the native nucleosome library to the reference standard.

An additional aspect of the present invention relates to a method for determining a prognosis for a subject having a disease or disorder associated with epigenetic modifications based on the quantification of one or more nucleosome modifications, the method comprising:
 a. isolating a biological sample from the subject;
 b. preparing a library of native mono- and/or polynucleosomes from the biological sample, wherein the library comprises nucleosomes comprising one or more core histone and/or DNA modifications in a target epitope(s);
 c. preparing a recombinant mono- and/or polynucleosome sample comprising nucleosomes carrying the one or more histone and/or DNA modification target epitopes;

d. providing the recombinant nucleosome sample at various concentrations to create a reference standard;
e. adding one or more affinity reagents to the native nucleosome library and recombinant nucleosome references;
f. performing an affinity reagent-based assay to measure the amount of nucleosome modification in the native nucleosome library and recombinant nucleosome reference standard;
g. quantifying the abundance of nucleosome modification in the target epitopes by comparing the relative abundance in the native nucleosome library to the reference standard; and
h. determining the prognosis of the subject based on the abundance of the one or more target epitopes.

Another aspect of the present invention relates to a method for identifying a biomarker of a disease or disorder associated with epigenetic modifications based on the quantification of one or more nucleosome modifications, the method comprising:
a. isolating a biological sample from the subject;
b. preparing a library of native mono- and/or polynucleosomes from the biological sample, wherein the library comprises nucleosomes comprising one or more core histone and/or DNA modifications in a target epitope(s);
c. preparing a recombinant mono- and/or polynucleosome sample comprising nucleosomes carrying the one or more histone and/or DNA modification target epitopes;
d. providing the recombinant nucleosome sample at various concentrations to create a reference standard;
e. adding one or more affinity reagents to the native nucleosome library and recombinant nucleosome references;
f. performing an affinity reagent-based assay to measure the amount of nucleosome modification in the native nucleosome library and recombinant nucleosome reference standard;
g. quantifying the abundance of nucleosome modification in the target epitopes by comparing the relative abundance in the native nucleosome library to the reference standard; and
h. correlating the abundance of the one or more target epitopes with the disease or disorder associated with epigenetic modifications; thereby identifying a biomarker of the disease or disorder associated with epigenetic modifications.

A further aspect of the present invention relates to a method of screening for an agent that modifies the epigenetic status of one or more nucleosome modifications from a biological sample of a subject, the method comprising determining the quantification of one or more nucleosome modifications in the presence and absence of the agent, wherein determining the quantification of the one or more nucleosome modifications comprises:
a. isolating a biological sample from the subject;
b. preparing a library of native mono- and/or polynucleosomes from the biological sample, wherein the library comprises nucleosomes comprising one or more core histone and/or DNA modifications in a target epitope(s);
c. preparing a recombinant mono- and/or polynucleosome sample comprising nucleosomes carrying the one or more histone and/or DNA modification target epitopes;
d. providing the recombinant nucleosome sample at various concentrations to create a reference standard;
e. adding one or more affinity reagents to the native nucleosome library and recombinant nucleosome references;
f. performing an affinity reagent-based assay to measure the amount of nucleosome modification in the native nucleosome library and recombinant nucleosome reference standard;
g. quantifying the abundance of nucleosome modification in the target epitopes by comparing the relative abundance in the native nucleosome library to the reference standard;
wherein a change in epigenetic status in the presence and absence of the agent identifies an agent that modifies the epigenetic status.

These and other aspects of the invention are set forth in more detail in the description of the invention below.

BRIEF DESCRIPTION OF THE DRAWINGS

FIGS. 3A-3C show optimization of ELISA to nucleosome PTMs using combinatorially modified dNucs. One capture antibody against a specific PTM (H3R8cit) was paired with a variety of detection antibodies, including (A) an anti-H3 C-terminal antibody, (B) an anti-H3R2cit antibody, and (C) the same anti-H3R8cit antibody used for capture. These capture-detection pairs were tested against a combinatorially modified dNuc (H3R2cit/R8cit/R17cit) and unmodified dNucs in ELISA to identify reagents with low background and high specificity.

DETAILED DESCRIPTION OF THE INVENTION

Figures 1A, 1B, 1C:
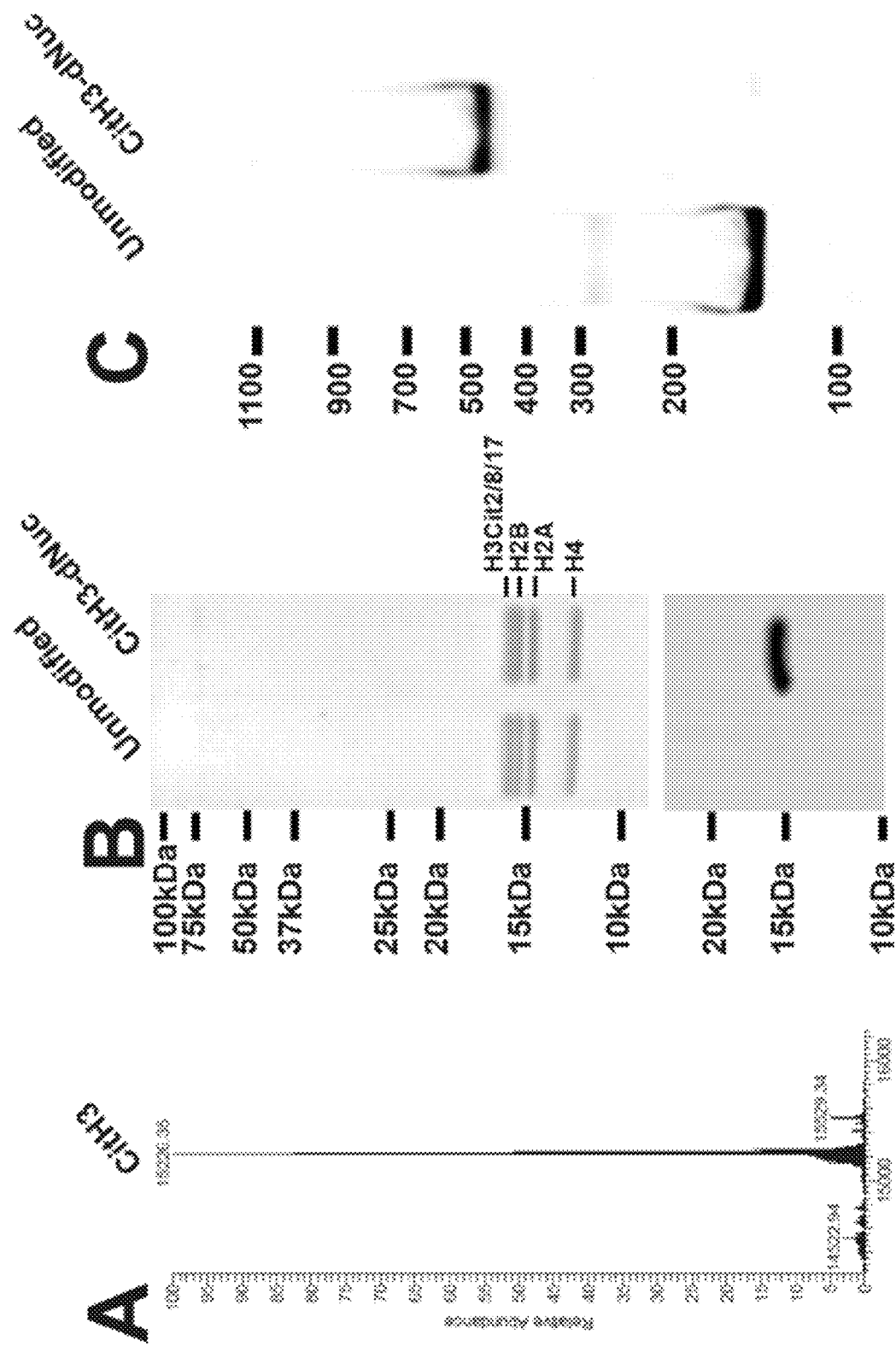
FIGS. 1A-1C show synthesis and quality validation of modified recombinant designer nucleosomes (dNucs). (A) Mass spectrometry of H3R2/R8/R17 tri-citrullinated histone prior to dNuc assembly. Expected mass=15227 Daltons; actual mass=15226 Daltons. (B) Octamer and PTM validation using Coomassie and immunoblot (Abcam: ab5103) after reducing SDS-PAGE. (C) Validation of H3R2cit/R8cit/R17cit dNuc assembly using native PAGE (no free DNA).

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of nucleosomes, and transiently and stably transfected cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consisting essentially of" as used herein in connection with a nucleic acid or protein means that the nucleic acid or protein does not contain any element other than the recited element(s) that significantly alters (e.g., more than about 1%, 5% or 10%) the function of interest of the nucleic acid or protein.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins, wherein the amino acid residues are linked by covalent peptide and/or pseudopeptide bonds.

A "nucleic acid" or "nucleotide sequence" is a sequence of nucleotide bases, and may be RNA, DNA or DNA-RNA hybrid sequences (including both naturally occurring and non-naturally occurring nucleotides), but is preferably either single or double stranded DNA sequences.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

By "substantially retain" a property, it is meant that at least about 75%, 85%, 90%, 95%, 97%, 98%, 99% or 100% of the property (e.g., activity or other measurable characteristic) is retained.

The term "epitope" refers to any site on a biomolecule that can evoke binding of an affinity reagent. The affinity reagent might recognize a linear sequence of a biomolecule or biomolecule fragment, the shape of biomolecule or biomolecule fragment, a chemo-physical property of a biomolecule or biomolecule fragment, or a combination of these.

"Amino acids" may be referred to herein by either their commonly known three letter symbols or by the one-letter symbols recommended by the IUPAC-IUB Biochemical Nomenclature Commission. Amino acid residues in proteins or peptides are abbreviated as follows: phenylalanine is Phe or F; leucine is Leu or L; isoleucine is Ile or I; methionine is Met or M; valine is Val or V; serine is Ser or S; proline is Pro or P; threonine is Thr or T; alanine is Ala or A; tyrosine is Tyr or Y; histidine is His or H; glutamine is Gln or Q; asparagine is Asn or N; lysine is Lys or K; aspartic acid is Asp or D; glutamic Acid is Glu or E; cysteine is Cys or C; tryptophan is Trp or W; arginine is Arg or R; and glycine is Gly or G.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., a carbon that is bound to a hydrogen, a carboxyl group, an amino group, and an R group, such as, homoserine, norleucine, methionine sulfoxide, and methionine methyl sulfonium. Such analogs have modified R groups (such as, norleucine) or modified peptide backbones, but retain the same basic chemical structure as a naturally occurring amino acid.

As to amino acid sequences, one of skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are known to those of skill in the art. Such conservatively modified variants are in addition to and do not exclude polymorphic variants, inter-species homologs/orthologs, and alleles of the agents described herein.

An "antigen" as used herein may be any structure which is recognized by an antibody or for which recognizing antibodies (or analogous affinity reagents such as aptamers or panned phage) can be raised. In certain embodiments, antigens may comprise a single amino acid residue or an amino acid fragment of 2 or more residues. In certain embodiments, antigens may comprise modifications of an amino acid, such as acetylation, methylation (e.g., mono-, di-, tri-, symmetric-, asymmetric-), phosphorylation, ubiquitination (e.g., mono-, di-, tri-, poly-), sumoylation, ADP-ribosylation, citrullination, biotinylation, and cis-trans isomerization. In certain embodiments, antigens may comprise nucleotide modifications, such as 5-methylcytosine. In other embodiments, antigens may comprise specific mutations, such as point mutations. In yet other embodiments, antigens may comprise wild-type amino acid sequences or nucleotide sequences.

The term "post-translational modification" refers to any modification of a natural or non-natural amino acid that occurs or would occur to such an amino acid after it has been incorporated into a polypeptide chain in vivo or in vitro. Such modifications include, but are not limited to, acylation (e.g., acetyl-, butyryl-, crotonyl-), methylation (e.g., mono-, di-, tri-), phosphorylation, ubiquitination (e.g., mono-, di-, tri-, poly-), sumoylation, ADP-ribosylation, citrullination, biotinylation, and cis-trans isomerization. Such modifications may be introduced synthetically, e.g., chemically, during polypeptide synthesis or enzymatically after polypeptide synthesis or polypeptide purification.

The term "post-transcriptional modification" refers to any modification of a natural or non-natural nucleotide that occurs or would occur to such a nucleotide after it has been incorporated into a polynucleotide chain in vivo or in vitro. Such modifications include, but are not limited to, 5-methylcyosine, 5-hydroxymethylcytosine, 5,6-dihydrouracil, 7-methylguanosine, xanthosine, and inosine.

The present invention relates to the use of recombinant/semi-synthetic nucleosomes carrying histone and/or DNA modifications as standards for assay quantification. Unlike the purified chromatin extracts in current use, the present assay utilizes fully defined recombinant/semi-synthetic nucleosomes for accurate quantification of single or combinatorial nucleosomal modifications. The methods of the invention advantageously are capable of providing absolute quantification of histone and/or DNA modifications, i.e., detection of the number of modified molecules rather than or in addition to relative abundance. Similar to standards commonly used in the art, modified nucleosomes will be assayed in the same experiment (treated identically to samples) to generate a standard curve for assay quantification. Quantification of single or combinatorial nucleosome PTMs may provide better biomarkers for disease than the relative measurements in current use. In some embodiments, the recombinant nucleosomes may be used as controls to confirm combinatorial modifications are detected on a single or adjacent nucleosomes.

As used herein, a recombinant nucleosome (also called a designer nucleosome (dNuc)) is one that has been prepared by bringing together histones (including the core histones H2A, H2B, H3, and H4, and optionally linker histone H1), DNA, and optionally other factors to form the nucleosome. In other words, a recombinant nucleosome is one that is synthesized, not isolated from cells or chromatin. Each histone in the nucleosome may be independently fully synthetic, semi-synthetic (e.g., recombinantly produced and ligated to a synthetic peptide), or recombinantly produced. Each histone in the nucleosome may be a histone variant (e.g., H3.3, H2A.Bbd, H2A.Z.1, H2A.Z.2, H2A.X, mH2A1.1, mH2A1.2, mH2A2, or TH2B). The term recombinant nucleosome encompasses semi-synthetic nucleosomes and synthetic nucleosomes.

The recombinant nucleosomes of the present invention may be used as spike-in standards in any known chromatin-based immunoassay (or that are based on an analogous affinity reagent).

Thus, one aspect of the present invention relates to a method for quantifying the abundance of a nucleosome modification (histone or DNA) in a biological sample, the method comprising:
 a. isolating a biological sample;
 b. preparing a library of native mono- and/or polynucleosomes from the biological sample, wherein the library comprises nucleosomes comprising one or more core histone and/or DNA modifications in a target epitope;
 c. preparing a recombinant mono- and/or polynucleosome sample comprising a core histone and/or DNA modification target epitope;

d. providing the recombinant nucleosome sample at various concentrations to create a reference standard;
e. adding an affinity reagent to the native nucleosome library and recombinant nucleosome references;
f. performing an affinity reagent-based assay to measure the amount of nucleosome modification in the native nucleosome library and the recombinant nucleosome reference standard; and
g. quantifying the abundance of nucleosome modification in the target epitope by comparing the relative abundance in the native nucleosome library to the reference standard.

Another aspect of the present invention relates to a method for quantifying the abundance of two or more modifications (histone or DNA) on a single nucleosome in a biological sample, the method comprising:
a. isolating a biological sample;
b. preparing a library of native mono- and/or polynucleosomes from the biological sample, wherein the library comprises nucleosomes comprising two or more core histone and/or DNA modifications in target epitopes;
c. preparing a recombinant mono- and/or polynucleosome sample comprising nucleosomes carrying the two or more histone and/or DNA modification target epitopes;
d. providing the recombinant nucleosome sample at various concentrations to create a reference standard;
e. adding two or more affinity reagents to the native nucleosome library and recombinant nucleosome references;
f. performing an affinity reagent-based assay to measure the amount of nucleosome modification in the native nucleosome library and recombinant nucleosome reference standard; and
g. quantifying the abundance of nucleosome modification in the target epitopes by comparing the relative abundance in the native nucleosome library to the reference standard.

A further aspect of the present invention relates to a method for quantifying the abundance of one or more nucleosome modifications (histone or DNA) in a biological sample from a subject having a disease or disorder, the method comprising:
a. isolating a biological sample from the subject;
b. preparing a library of native mono- and/or polynucleosomes from the biological sample, wherein the library comprises nucleosomes comprising one or more core histone and/or DNA modifications in a target epitope(s);
c. preparing a recombinant mono- and/or polynucleosome sample comprising nucleosomes carrying the one or more histone and/or DNA modification target epitopes;
d. providing the recombinant nucleosome sample at various concentrations to create a reference standard;
e. adding one or more affinity reagents to the native nucleosome library and recombinant nucleosome references;
f. performing an affinity reagent-based assay to measure the amount of nucleosome modification in the native nucleosome library and recombinant nucleosome reference standard; and
g. quantifying the abundance of nucleosome modification in the target epitope by comparing the relative abundance in the native nucleosome library to the reference standard.

In each of the methods of the invention, the biological sample may be any sample from which nucleosomes can be isolated. The biological sample may be, for example, blood, serum, plasma, urine, saliva, semen, prostatic fluid, nipple aspirate, lachrymal fluid, perspiration, feces, cheek swabs, cerebrospinal fluid, cell lysate samples, amniotic fluid, gastrointestinal fluid, biopsy tissue, lymphatic fluid, or cerebrospinal fluid. In some embodiments, the biological sample comprises cells and the chromatin is isolated from the cells. In some embodiments, the cells are cells from a disease of disorder associated with changes in one or more histone post-translational modifications and/or DNA modifications, e.g., a diseased cell. In some embodiments, the cells are cells from a tissue or organ affected by a disease or disorder associated with mutations in histones, e.g., a diseased tissue or organ. The cells may be obtained from the diseased organ or tissue by any means known in the art, including but not limited to biopsy, aspiration, and surgery.

In other embodiments, the cells are not cells from a tissue or organ affected by a disease or disorder associated with changes in histone post-translational modifications or DNA modifications or associated with mutations in histones. The cells may be, e.g., cells that serve as a proxy for the diseased cells. The cells may be cells that are more readily accessible than the diseased cells, e.g., that can be obtained without the need for complicated or painful procedures such as biopsies. Examples of suitable cells include, without limitation, peripheral blood mononuclear cells.

In some embodiments, the biological sample is a biopsy. In other embodiments, the biological sample is a biological fluid. In some embodiments, the biological sample comprises peripheral blood mononuclear cells. In other embodiments, the biological sample comprises circulating nucleosomes, e.g., as released from dying cells. The circulating nucleosomes may be, e.g., from blood or from cells from a disease or disorder associated with epigenetic modifications. In certain embodiments, the biological sample is plasma, urine, saliva, stool, lymphatic fluid, or cerebrospinal fluid. In some embodiments, the biological sample may be treated with an enzyme to digest chromatin into mono- and/or polynucleosomes. The enzyme may be, without limitation, a nuclease, e.g., micrococcal nuclease.

The subject may be any subject for which the methods of the present invention are desired. In some embodiments, the subject is a mammal, e.g., a human. In some embodiments, the subject is a laboratory animal, e.g., a mouse, rat, dog, or monkey, e.g., an animal model of a disease. In certain embodiments, the subject may be one that has been diagnosed with or is suspected of having a disease or disorder. In some embodiments, the subject may be one that is at risk for developing a disease or disorder, e.g., due to genetics, family history, exposure to toxins, etc.

The affinity agent used in the methods of the invention may be any agent that specifically recognizes and binds to a histone or DNA modification of interest present in a target epitope. In some embodiments, the affinity agent is an antibody or antibody fragment directed towards the epitope. The antibody or fragment thereof may be a full-length immunoglobulin molecule, an Fab, an Fab', an F(ab)'$_2$, an scFv, an Fv fragment, a nanobody, a VHH or a minimal recognition unit. The affinity agent may be an aptamer or a non-immunoglobulin scaffold such as an affibody, an affilin molecule, an AdNectin, a lipocalin mutein, a DARPin, a Knottin, a Kunitz-type domain, an Avimer, a Tetranectin or a trans-body.

In some embodiments, the quantification of at least one or more nucleosome modification(s) is determined by an antibody-based detection assay. Examples of antibody-based detection methods include, without limitation, ChIP, ELISA, AlphaLISA, AlphaSCREEN, Luminex, and immunoblotting. In some embodiments, the antibody-based detection assay uses two different antibodies for substrate capture and detection. In one embodiment, the capture and detection antibodies may specifically bind to a histone PTM and another nucleosome structure, such as DNA or unmodified histone, respectively (as shown in FIG. 3A). In another embodiment, the capture and detection antibodies are to two different histone PTMs, respectively (as shown in FIG. 3B). In some embodiments, the antibody-based detection assay uses the same antibody for both substrate capture and detection (as shown in FIG. 3C).

The histone or DNA modification that may be quantitated by the methods of the invention include any modification that is known in the art or identified in the future. Known post-translational amino acid modifications include, without limitation, N-acetylation of serine and alanine; phosphorylation of serine, threonine and tyrosine; N-crotonylation, N-acylation of lysine; N6-methylation, N6,N6-dimethylation, N6,N6,N6-trimethylation of lysine; omega-N-methylation, symmetrical-dimethylation, asymmetrical-dimethylation of arginine; citrullination of arginine; ubiquitinylation of lysine; sumoylation of lysine; O-methylation of serine and threonine, ADP-ribosylation of arginine, aspartic acid and glutamic acid; and oncogenic mutations (e.g., H3K4M, H3K9M, H3K27M, H3G34R, H3G34V, H3G34W, or H3K36M). Known post-transcriptional DNA modifications include, without limitation, 5-methylcytosine, 5-hydroxymethylcytosine, 5-formylcytosine, 5-carboxylcytosine, 3-methylcytosine, 5,6-dihydrouracil, 7-methylguanosine, xanthosine, and inosine.

The target epitope may be any epitope on a core histone or on DNA for which quantitation and/or monitoring is desired. In some embodiments, the epitope is a post-translational modification or protein isoform. In some embodiments, the epitope of the core histone comprises at least one post-translational amino acid modification, e.g., selected from the group consisting of N-acetylation of serine and alanine; phosphorylation of serine, threonine and tyrosine; N-acylation of lysine (e.g., crotonylation or butyrylation); N6-methylation, N6,N6-dimethylation, N6,N6,N6-trimethylation of lysine; omega-N-methylation, symmetrical-dimethylation, asymmetrical-dimethylation of arginine; citrullination of arginine; ubiquitinylation of lysine; sumoylation of lysine; O-methylation of serine and threonine; phosphorylation of serine, threonine or tyrosine; ADP-ribosylation of arginine, aspartic acid and glutamic acid, and any combination thereof. The modification may be any of those in listed in Table 1(a)-1(f), either singly or in any combination.

In some embodiments, the epitope is a mutation in a core histone, e.g., a mutation associated with a disease or disorder. In some embodiments, the mutation is an oncogenic mutation, e.g., a mutation including, but not limited to, H3K4M, H3K9M, H3K27M, H3G34R, H3G34V, H3G34W, H3K36M, and any combination thereof. The H3 mutants may be based on any variant backbone of H3, e.g., H3.1, H3.2, or H3.3.

An additional aspect of the present invention relates to a method for determining a prognosis for a subject having a disease or disorder associated with epigenetic modifications based on the quantification of one or more nucleosome modifications, the method comprising:

a. isolating a biological sample from the subject;
b. preparing a library of native mono- and/or polynucleosomes from the biological sample, wherein the library comprises nucleosomes comprising one or more core histone and/or DNA modifications in a target epitope(s);
c. preparing a recombinant mono- and/or polynucleosome sample comprising nucleosomes carrying the one or more histone and/or DNA modification target epitopes;
d. providing the recombinant nucleosome sample at various concentrations to create a reference standard;
e. adding one or more affinity reagents to the native nucleosome library and recombinant nucleosome references;
f. performing an affinity reagent-based assay to measure the amount of nucleosome modification in the native nucleosome library and recombinant nucleosome reference standard;
g. quantifying the abundance of nucleosome modification in the target epitopes by comparing the relative abundance in the native nucleosome library to the reference standard; and
h. determining the prognosis of the subject based on the abundance of the one or more target epitopes.

The details described above for the method of detecting and quantitating the presence of nucleosome modifications apply to this method as well.

In some instances, the epigenetic status of an epitope is indicative of the prognosis of a disease or disorder associated with epigenetic modifications. Thus, a determination of the epigenetic status of an epitope in a subject that has been diagnosed with or is suspected of having a disease or disorder associated with epigenetic modifications may be useful to determine the prognosis for the subject. Many such examples are known in the art. One example is prostate cancer and histone PTMs, including, without limitation, increased H3K18 acetylation and H3K4 dimethylation associated with a significantly higher risk of prostate tumor recurrence, H4K12 acetylation and H4R3 dimethylation correlated with tumor stage, and H3K9 dimethylation associated with low-grade prostate cancer patients at risk for tumor recurrence. Another example is the link between overall survival in breast cancer patients and methylation status of CpGs in the genes CREB5, EXPH5, ZNF775, ADCY3, and ADMA8. Another example is glioblastoma and hypermethylation of intronic regions of genes like EGFR, PTEN, NF1, PIK3R1, RB1, PDGFRA, and QKI. A further example is inferior prognosis for colon cancer and methylation status of the promoter of the CNRIP1, FBN1, INA, MAL, SNCA, and SPG20 genes.

Another aspect of the present invention relates to a method for identifying a biomarker of a disease or disorder associated with epigenetic modifications based on the quantification of one or more nucleosome modifications, the method comprising:

a. isolating a biological sample from the subject;
b. preparing a library of native mono- and/or polynucleosomes from the biological sample, wherein the library comprises nucleosomes comprising one or more core histone and/or DNA modifications in a target epitope(s);
c. preparing a recombinant mono- and/or polynucleosome sample comprising nucleosomes carrying the one or more histone and/or DNA modification target epitopes;
d. providing the recombinant nucleosome sample at various concentrations to create a reference standard;
e. adding one or more affinity reagents to the native nucleosome library and recombinant nucleosome references;
f. performing an affinity reagent-based assay to measure the amount of nucleosome modification in the native nucleosome library and recombinant nucleosome reference standard;

g. quantifying the abundance of nucleosome modification in the target epitopes by comparing the relative abundance in the native nucleosome library to the reference standard; and h. correlating the abundance of the one or more target epitopes with the disease or disorder associated with epigenetic modifications; thereby identifying a biomarker of the disease or disorder associated with epigenetic modifications.

The details described above for the method of detecting and quantitating the presence of a nucleosome modification apply to this method as well.

In this method, biological samples of diseased tissue may be taken from a number of patients have a disease or disorder and the epigenetic status of one or more epitopes determined. Correlations between the epitope status and the occurrence, stage, subtype, prognosis, etc., may then be identified using analytical techniques that are well known in the art.

A further aspect of the present invention relates to a method of screening for an agent that modifies the epigenetic status of one or more nucleosome modifications from a biological sample of a subject, the method comprising determining the quantification of one or more nucleosome modifications in the presence and absence of the agent, wherein determining the quantification of the one or more nucleosome modifications comprises:

a. isolating a biological sample from the subject;

b. preparing a library of native mono- and/or polynucleosomes from the biological sample, wherein the library comprises nucleosomes comprising one or more core histone and/or DNA modifications in a target epitope(s);

c. preparing a recombinant mono- and/or polynucleosome sample comprising nucleosomes carrying the one or more histone and/or DNA modification target epitopes;

d. providing the recombinant nucleosome sample at various concentrations to create a reference standard;

e. adding one or more affinity reagents to the native nucleosome library and recombinant nucleosome references;

f. performing an affinity reagent-based assay to measure the amount of nucleosome modification in the native nucleosome library and recombinant nucleosome reference standard;

g. quantifying the abundance of nucleosome modification in the target epitopes by comparing the relative abundance in the native nucleosome library to the reference standard;

wherein a change in epigenetic status in the presence and absence of the agent identifies an agent that modifies the epigenetic status.

The details described above for the method of detecting and quantitating the presence of a nucleosome modification apply to this method as well.

The screening method may be used to identify agents that increase or decrease epigenetic modifications. In some embodiments, the detected increase or decrease is statistically significant, e.g., at least p<0.05, e.g., p<0.01, 0.005, or 0.001. In other embodiments, the detected increase or decrease is at least about 10%, 20%, 30%, 40%, 50%, 60%, 70%, 80%, 90%, 100% or more.

Any compound of interest can be screened according to the present invention. Suitable test compounds include organic and inorganic molecules. Suitable organic molecules can include but are not limited to small molecules (compounds less than about 1000 Daltons), polypeptides (including enzymes, antibodies, and antibody fragments), carbohydrates, lipids, coenzymes, and nucleic acid molecules (including DNA, RNA, and chimeras and analogs thereof) and nucleotides and nucleotide analogs.

Further, the methods of the invention can be practiced to screen a library of potential or targeted regulators, e.g., a small molecule library, a combinatorial chemical compound library, a polypeptide library, a cDNA library, a library of antisense nucleic acids, an siRNA library, and the like, or an arrayed collection of compounds such as polypeptide and nucleic acid arrays.

Any suitable screening assay format may be used, e.g., high throughput screening.

The method may also be used to characterize agents that have been identified as an agent that modifies the epigenetic status of a specific genomic locus in chromatin. Characterization, e.g., preclinical characterization, may include, for example, determining effective concentrations, determining effective dosage schedules, and measuring pharmacokinetics and pharmacodynamics.

A further aspect of the invention relates to a method for monitoring changes in epigenetic status over time in chromatin from a biological sample of a subject, using the methods of the invention.

The details described above for the method of detecting and quantitating the presence of a nucleosome modification apply to this method as well.

The steps of the method may be repeated as many times as desired to monitor changes in the status of an epigenetic modification, e.g., 2, 3, 4, 5, 6, 7, 8, 9, 10, 25, 50, or 100 or more times. The method may be repeated on a regular schedule (e.g., daily, weekly, monthly, yearly) or on an as needed basis. The method may be repeated, for example, before, during, and/or after therapeutic treatment of a subject; after diagnosis of a disease or disorder in a subject; as part of determining a diagnosis of a disease or disorder in a subject; after identification of a subject as being at risk for development of a disease or disorder, or any other situation where it is desirable to monitor possible changes in epigenetic modifications or mutations.

An additional aspect of the invention relates to a method for monitoring the effectiveness of an epigenetic therapy in a subject having a disease or disorder associated with epigenetic modifications, the method comprising monitoring changes in epigenetic status over time in chromatin from a biological sample of the subject, using the methods of the invention.

The details described above for the method of detecting and quantitating the presence of a nucleosome modification apply to this method as well.

Epigenetic therapies are those designed to alter the epigenetic status of proteins (e.g., histones) or DNA. One example of an epigenetic therapy includes lysine deacetylase inhibitors (also termed histone deacetylase inhibitors) (e.g., vorinostat (suberoylanilide hydroxamic acid), CI-994 (tacedinaline), MS-275 (entinostat), BMP-210, M344, NVP-LAQ824, LBH-529 (panobinostat), MGCD0103 (mocetinostat), PXD101 (belinostat), CBHA, PCI-24781, ITF2357, valproic acid, trichostatin A, and sodium butyrate), which are used to treat cutaneous T-cell lymphoma (CTCL) or in clinical trials for the treatment of hematologic and solid tumors, including lung, breast, pancreas, renal, and bladder cancers, melanoma, glioblastoma, leukemias, lymphomas, and multiple myeloma. A further example of an epigenetic therapy is lysine acetyltransferase inhibitors (also termed histone acetyltransferase inhibitors) (e.g., epigallocatechin-3-gallate, garcinol, anacardic acid, CPTH2, curcumin, MB-3, MG149, C646, and romidepsin). Another example of an epigenetic therapy is DNA methyltransferase inhibitors (e.g., azacytidine, decitabine, zebularine, caffeic acid, chlorogenic acid, epigallocatechin, hydralazine, procainamide, procaine, and RG108), which have been approved for treatment of acute myeloid leukemia, myelodysplastic syndrome, and chronic myelomonocytic leukemia and in clinical trials for treatment of solid tumors. Other epigenetic therapies include, without limitation, lysine methyltransferases (e.g., pinometostat, tazometostat, CPI-1205); lysine demethylases (e.g., ORY1001); arginine methyltransferases (e.g., EPZ020411); arginine deiminases (e.g., GSK484); and isocitrate dehydrogenases (e.g., enasidenib, ivosidenib). See Fischle et al., *ACS Chem. Biol.* 11:689 (2016); DeWoskin et al., *Nature Rev.* 12:661 (2013); Campbell et al., *J. Clin. Invest.* 124:64 (2014); and Brown et al., *Future Med. Chem.* 7:1901 (2015); each incorporated by reference herein in its entirety.

The steps of the method may be repeated as many times as desired to monitor effectiveness of the treatment, e.g., 2, 3, 4, 5, 6, 7, 8, 9, 10, 25, 50, or 100 or more times. The method may be repeated on a regular schedule (e.g., daily, weekly, monthly, yearly) or on an as needed basis, e.g., until the therapeutic treatment is ended. The method may be repeated, for example, before, during, and/or after therapeutic treatment of a subject, e.g., after each administration of the treatment. In some embodiments, the treatment is continued until the method of the invention shows that the treatment has been effective.

Another aspect of the invention relates to a method for selecting a suitable treatment for a subject having a disease or disorder associated with epigenetic modifications based on the epigenetic status in chromatin from a biological sample of the subject, using the methods of the invention.

The details described above for the method of detecting and quantitating the presence of a nucleosome modification or a mutation apply to this method as well.

The method may be applied, for example, to subjects that have been diagnosed or are suspected of having a disease or disorder associated with epigenetic modifications. A determination of the epigenetic status of an epitope may indicate that the status of an epitope has been modified and an epigenetic therapy should be administered to the subject to correct the modification. Conversely, a determination that the status of an epitope has not been modified would indicate that an epigenetic therapy would not be expected to be effective and should be avoided. For example, a determination that a particular acetylated histone residue (H3K27ac) has been deacetylated may indicate that treatment with a lysine deacetylase inhibitor would be appropriate. Similarly, a determination that a particular methylated histone residue (H3K27me3) has been hypermethylated may indicate that treatment with a lysine methyltransferase inhibitor would be appropriate.

As used herein, a disease or disorder associated with epigenetic modifications is any disease or disorder in which an epigenetic modification is known to be the cause of the disease or disorder or at least one symptom of the disease or disorder or a disease or disorder in which an epigenetic modification is a biomarker of the disease or disorder. In any of the methods of the invention, the disease or disorder associated with epigenetic modifications or mutations may be a cancer, a central nervous system (CNS) disorder, an autoimmune disorder, an inflammatory disorder, or an infectious disease.

The cancer may be any benign or malignant abnormal growth of cells, including but not limited to acoustic neuroma, acute granulocytic leukemia, acute lymphocytic leukemia, acute myelogenous leukemia, adenocarcinoma, adrenal carcinoma, adrenal cortex carcinoma, anal cancer, anaplastic astrocytoma, angiosarcoma, basal cell carcinoma, bile duct carcinoma, bladder cancer, brain cancer, breast cancer, bronchogenic carcinoma, cervical carcinoma, cervical hyperplasia, chordoma, choriocarcinoma, chronic granulocytic leukemia, chronic lymphocytic leukemia, chronic myelogenous leukemia, colon cancer, colorectal cancer, craniopharyngioma, cystadenosarcoma, embryonic carcinoma, endometrium cancer, endotheliosarcoma, ependymoma, epithelial carcinoma, esophageal carcinoma, essential thrombocytosis, Ewing's tumor, fibrosarcoma, genitourinary carcinoma, glioblastoma, glioma, gliosarcoma, hairy cell leukemia, head and neck cancer, hemangioblastoma, hepatic carcinoma, Hodgkin's disease, Kaposi's sarcoma, leiomyosarcoma, leukemia, liposarcoma, lung cancer, lymphangioendotheliosarcoma, lymphangiosarcoma, lymphoma, malignant carcinoid carcinoma, malignant hypercalcemia, malignant melanoma, malignant pancreatic insulinoma, mastocytoma, medullar carcinoma, medulloblastoma, melanoma, meningioma, mesothelioma, multiple myeloma, mycosis fungoides, myeloma, myxoma, myxosarcoma, neuroblastoma, non-Hodgkin's lymphoma, non-small cell lung carcinoma, oligodendroglioma, osteogenic sarcoma, ovarian cancer, pancreatic cancer, papillary adenosarcoma, papillary sarcoma, pinealoma, polycythemia vera, primary brain carcinoma, primary macroglobulinemia, prostate cancer, rectal cancer, renal cell carcinoma, retinoblastoma, rhabdomyosarcoma, sebaceous gland sarcoma, seminoma, skin cancer, small cell lung carcinoma, soft-tissue sarcoma, squamous cell carcinoma, stomach carcinoma, sweat gland carcinoma, synovioma, testicular carcinoma, throat cancer, thyroid carcinoma, and Wilms' tumor.

CNS disorders include genetic disorders, neurodegenerative disorders, psychiatric disorders, and tumors. Illustrative diseases of the CNS include, but are not limited to, Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder, mania, manic psychosis,), schizophrenia, schizoaffective disorder, schizophreniform disorder, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions, psychosis not otherwise specified (Psychosis NOS),), dementia, aging, paranoia, attention deficit disorder, psychosexual disorders, sleeping disorders, pain disorders, eating or weight disorders (e.g., obesity, cachexia, anorexia nervosa, and bulemia), ophthalmic disorders involving the retina, posterior tract, and optic nerve (e.g., retinitis pigmentosa, diabetic retinopathy and other retinal degenerative diseases, uveitis, age-related macular degeneration, glaucoma), and cancers and tumors (e.g., pituitary tumors) of the CNS.

Autoimmune and inflammatory diseases and disorders include, without limitation, myocarditis, postmyocardial infarction syndrome, postpericardiotomy syndrome, Sub-acute bacterial endocarditis, anti-glomerular basement membrane nephritis, interstitial cystitis, lupus nephritis, autoimmune hepatitis, primary biliary cirrhosis, primary sclerosing cholangitis, antisynthetase syndrome, sinusitis, periodontitis, atherosclerosis, dermatitis, allergy, allergic rhinitis, allergic airway inflammation, chronic obstructive pulmonary disease, eosinophilic pneumonia, eosinophilic esophagitis, hypereosinophilic syndrome, graft-versus-host disease, atopic dermatitis, tuberculosis, asthma, chronic peptic ulcer, alopecia areata, autoimmune angioedema, autoimmune progesterone dermatitis, autoimmune urticaria, bullous pemphigoid, cicatricial pemphigoid, dermatitis herpetiformis, discoid lupus erythematosus, epidermolysis bullosa acquisita, erythema nodosum, gestational pemphigoid, hidradenitis suppurativa, lichen planus, lichen sclerosus, linear IgA disease, morphea, pemphigus vulgaris, pityriasis lichenoides et varioliformis acuta, Mucha-Habermann disease, psoriasis, systemic scleroderma, vitiligo, Addison's disease, autoimmune polyendocrine syndrome type 1, autoimmune polyendocrine syndrome type 2, autoimmune polyendocrine syndrome type 3, autoimmune pancreatitis, diabetes mellitus type 1, autoimmune thyroiditis, Ord's thyroiditis, Graves' disease, autoimmune oophoritis, endometriosis, autoimmune orchitis, Sjogren's syndrome, autoimmune enteropathy, celiac disease, Crohn's disease, irritable bowel syndrome, diverticulitis, microscopic colitis, ulcerative colitis, antiphospholipid syndrome, aplastic anemia, autoimmune hemolytic anemia, autoimmune lymphoproliferative syndrome, autoimmune neutropenia, autoimmune thrombocytopenic purpura, cold agglutinin disease, essential mixed cryoglobulinemia, Evans syndrome, pernicious anemia, pure red cell aplasia, thrombocytopenia, adiposis dolorosa, adult-onset Still's disease, ankylosing spondylitis, CREST syndrome, drug-induced lupus, enthesitis-related arthritis, eosinophilic fasciitis, Felty syndrome, IgG4-related disease, juvenile arthritis, Lyme disease (chronic), mixed connective tissue disease, palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, systemic lupus erythematosus, undifferentiated connective tissue disease, dermatomyositis, fibromyalgia, myositis, myasthenia gravis, neuromyotonia, paraneoplastic cerebellar degeneration, polymyositis, acute disseminated encephalomyelitis, acute motor axonal neuropathy, anti-N-methyl-D-aspartate receptor encephalitis, Balo concentric sclerosis, Bickerstaff's encephalitis, chronic inflammatory demyelinating polyneuropathy, Guillain-Barré syndrome, Hashimoto's encephalopathy, idiopathic inflammatory demyelinating diseases, Lambert-Eaton myasthenic syndrome, multiple sclerosis, Oshtoran syndrome, pediatric autoimmune neuropsychiatric disorder associated with *Streptococcus* (PANDAS), progressive inflammatory neuropathy, restless leg syndrome, stiff person syndrome, Sydenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease, Ménière's disease, Behçet's disease, eosinophilic granulomatosis with polyangiitis, giant cell arteritis, granulomatosis with polyangiitis, IgA vasculitis, Kawasaki's disease, leukocytoclastic vasculitis, lupus vasculitis, rheumatoid vasculitis, microscopic polyangiitis, polyarteritis nodosa, polymyalgia rheumatic, urticarial vasculitis, vasculitis, and primary immune deficiency.

The term "infectious diseases," as used herein, refers to any disease associated with infection by an infectious agent. Examples of infectious agents include, without limitation, viruses and microorganisms (e.g., bacteria, parasites, protozoans, cryptosporidiums). Viruses include, without limitation, Hepadnaviridae including hepatitis A, B, C, D, E, F, G, etc.; Flaviviridae including human hepatitis C virus (HCV), yellow fever virus and dengue viruses; Retroviridae including human immunodeficiency viruses (HIV) and human T lymphotropic viruses (HTLV1 and HTLV2); Herpesviridae including herpes simplex viruses (HSV-1 and HSV-2), Epstein Barr virus (EBV), cytomegalovirus, varicella-zoster virus (VZV), human herpes 6 (HHV-6) human herpes virus 8 (HHV-8), and herpes B virus; Papovaviridae including human papilloma viruses; Rhabdoviridae including rabies virus; Paramyxoviridae including respiratory syncytial virus; Reoviridae including rotaviruses; Bunyaviridae including hantaviruses; Filoviridae including Ebola virus; Adenoviridae; Parvoviridae including parvovirus B-19; Arenaviridae including Lassa virus; Orthomyxoviridae including influenza viruses; Poxviridae including Orf virus, molluscum contageosum virus, smallpox virus and Monkey pox virus; Togaviridae including Venezuelan equine encephalitis virus; Coronaviridae including corona viruses such as the severe acute respiratory syndrome (SARS) virus; and Picornaviridae including polioviruses; rhinoviruses; orbiviruses; picodnaviruses; encephalomyocarditis virus (EMV); Parainfluenza viruses, adenoviruses, Coxsackieviruses, Echoviruses, Rubeola virus, Rubella virus, human papillomaviruses, Canine distemper virus, Canine contagious hepatitis virus, Feline calicivirus, Feline rhinotracheitis virus, TGE virus (swine), Foot and mouth disease virus, simian virus 5, human parainfluenza virus type 2, human metapneuomovirus, enteroviruses, and any other pathogenic virus now known or later identified (see, e.g., *Fundamental Virology*, Fields et al., Eds., 3$^{rd}$ ed Lippincott-Raven, New York, 1996, the entire contents of which are incorporated by reference herein for the teachings of pathogenic viruses).

Pathogenic microorganisms include, but are not limited to, *Rickettsia, Chlamydia, Chlamydophila*, Mycobacteria, Clostridia, Corynebacteria, *Mycoplasma, Ureaplasma, Legionella, Shigella, Salmonella*, pathogenic *Escherichia coli* species, *Bordatella, Neisseria, Treponema, Bacillus, Haemophilus, Moraxella, Vibrio, Staphylococcus* spp., *Streptococcus* spp., *Campylobacter* spp., *Borrelia* spp., *Leptospira* spp., *Erlichia* spp., *Klebsiella* spp., *Pseudomonas* spp., *Helicobacter* spp., and any other pathogenic microorganism now known or later identified (see, e.g., Microbiology, Davis et al, Eds., 4$^{th}$ ed., Lippincott, N.Y., 1990, the entire contents of which are incorporated herein by reference for the teachings of pathogenic microorganisms). Specific examples of microorganisms include, but are not limited to, *Helicobacter pylori, Chlamydia pneumoniae, Chlamydia trachomatis, Ureaplasma urealyticum, Mycoplasma pneumoniae, Staphylococcus aureus, Streptococcus pyogenes, Streptococcus pneumoniae, Streptococcus viridans, Enterococcus faecalis, Neisseria meningitidis, Neisseria gonorrhoeae, Treponema pallidum, Bacillus anthracis, Salmonella typhi, Vibrio cholera, Pasteurella pestis (Yersinia pestis), Pseudomonas aeruginosa, Campylobacter jejuni, Clostridium difficile, Clostridium botulinum, Mycobacterium tuberculosis, Borrelia burgdorferi, Haemophilus ducreyi, Corynebacterium diphtheria, Bordetella pertussis, Bordetella parapertussis, Bordetella bronchiseptica, Haemophilus influenza, Listeria monocytogenes, Shigella flexneri, Anaplasma phagocytophilum*, enterotoxic *Escherichia coli*, and *Schistosoma haematobium*.

Another aspect of the invention relates to methods of determining the specificity of a detection reagent (e.g., an antibody or fragment thereof, an aptamer, etc.) for a core histone and/or DNA modification target epitope, comprising using the recombinant mono- and/or polynucleosome sample of the invention comprising the core histone and/or DNA modification target epitope.

In some embodiments, the disease or disorder includes, but is not limited to, obesity, diabetes, heart disease, autism, fragile X syndrome, ATR-X syndrome, Angelman syndrome, Prader-Willi syndrome, Beckwith Wiedemann syndrome, Rett syndrome, Rubinstein-Taybi syndrome, Coffin-Lowry syndrome Immunodeficiency-centrometric instability-facial anomalies syndrome, α-thalassaemia, leukemia, Cornelia de Langue syndrome, Kabuki syndrome, progressive systemic sclerosis, and cardiac hypertrophy.

In some embodiments, the disease or disorder associated with epigenetic modifications is selected form the group consisting of renal cell carcinoma, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullar carcinoma, mastocytoma, mesothelioma, synovioma, melanoma, leiomyosarcoma, rhabdomyosarcoma, neuroblastoma, retinoblastoma, glioblastoma, oligodendroglioma, acoustic neuroma, hemangioblastoma, meningioma, pinealoma, ependymoma, craniopharyngioma, epithelial carcinoma, embryonic carcinoma, squamous cell carcinoma, base cell carcinoma, fibrosarcoma, myxoma, myxosarcoma, glioma, liposarcoma, infections caused by *Helicobacter pylori*, *Listeria monocytogenes*, *Shigella flexneri*, *Anaplasma phagocytophilum*, *Chlamydophila*, Epstein-Barr Virus, herpes, HIV, *Schistosoma haematobium*; Obesity, diabetes, heart disease; autism, fragile X syndrome, ATR-X syndrome, Angelman syndrome, Prader-Willi syndrome, Beckwith Wiedemann syndrome, Rett syndrome, Rubinstein-Taybi syndrome, Coffin-Lowry syndrome Immunodeficiency-centrometric instability-facial anomalies syndrome, α-thalassaemia, leukemia, Huntington's disease, schizophrenia, bipolar disease, aging, dementia, Alzheimer's disease, Parkinson's disease, Cornelia de Langue syndrome, Kabuki syndrome, Sjogren's syndrome, Vitiligo, progressive systemic sclerosis, psoriasis, primary biliary cirrhosis, Crohn's disease and ulcerative colitis, Hashimoto's thyroiditis, Grave's disease, inflammatory bowel disease, atherosclerosis, and cardiac hypertrophy.

Another aspect of the invention provides reagents and kits including reagents for carrying out one of the methods described herein. The reagents may be included in suitable packages or containers. The kit may include one or more reagents containing recombinant nucleosomes as described herein for the quantification of epitopes, for example in antibody-based detection assays. The kit may also include at least one affinity reagent as described herein, for example an antibody or a fragment or variant thereof.

In some embodiments, the recombinant nucleosomes include DNA-protein complexes made with histones, histone isoforms, histone post-translational modifications, or histone mutations. In various embodiments, any variant of core histone sequences, which are known in the art, or post-translational modification, including those defined in Tables 1(a)-1(f), can be installed on the histones that comprise the histone octamer. In one embodiment, a set of recombinant nucleosomes is provided.

In other embodiments, the kit may include one or more wash buffers, (for example, phosphate buffered saline) and/or other buffers in packages or containers. The kit may also include reagents necessary for the measurement of the amount of captured standard or sample.

When a kit is supplied, the different components may be packaged in separate containers and admixed immediately before use. Such packaging of the components separately may permit long-term storage without losing the active components' functions. Kits may also be supplied with instructional materials. Instructions may be printed on paper or other substrate, and/or may be supplied as an electronic-readable medium.

In some embodiments, the kit may comprise a panel of standards that represent some or all of the different possibilities of a particular class of PTM, e.g., lysine methylation, lysine acylation, or arginine methylation, e.g., of a single histone or multiple histones. The panel may include some or all of the modifications considered to be relevant to one or more diseases. In some embodiments, the kit may comprise a set of standards that represent most or all of the different possibilities of histone mutations, e.g., oncogenic histone mutations, e.g., of a single histone or multiple histones. The panels may be used to assess the specificity of affinity reagents, monitor technical variability, and normalize experiments.

Having described the present invention, the same will be explained in greater detail in the following examples, which are included herein for illustration purposes only, and which are not intended to be limiting to the invention.

EXAMPLES

Example 1: Synthesis and Quality Validation of Modified Recombinant Designer Nucleosomes (dNucs)

Recombinant dNucs are ideal ELISA standards as they are highly defined and mimic the endogenous antibody target. FIGS. 1A-1C show representative quality metrics for dNuc assembly. In this example, a H3R2/R8/R17 tri-citrullinated histone (H3R2cit/R8cit/R17cit) was generated using a native chemical ligation approach based on published methods (Chen et al., *Chembiochem* 15(14): 2071 (2014)). The resulting modified histone was >95% pure by analytical HPLC and within one Dalton of expected mass by high-resolution mass spectrometry (FIG. 1A). To generate citrullinated dNucs, the unmodified histone H3 subunit was replaced with H3R2cit/R8cit/R17cit histones during octamer assembly. As expected, the resulting dNuc was immunoreactive with an anti-citrullinated histone (H3R2cit/R8cit/R17cit) antibody (FIG. 1B; top) and displayed equal stoichiometric ratios of histones (FIG. 1B; bottom) and no detectable free DNA (FIG. 1C). These data show that recombinant dNucs are highly pure, making them exceptional standards for ELISAs that aim to quantify histone PTMs.

Example 2: Nucleosomes are Recovered at Expected Values and Provide Reliable Calibration in Human Plasma Recent advances in cell-free nucleosome (CFN) analysis have made non-invasive, chromatin-targeted liquid biopsies a potential reality (Holdenrieder et al., *Int. J. Cancer* 95(2): 114 (2001); Holdenrieder et al., *Ann. NY Acad. Sci.* 1137: 180 (2008); Rumore et al., *J. Clin. Invest.* 86(1):69 (1990); Holdenrieder et al., *Clin. Chem.* 51(8):1544 (2005)). However, existing assays for nucleosome PTM quantification typically use modified histone subunits as assay standards. These fail to recapitulate binding characteristics of native chromatin, and thus can only provide relative measurements when used as in-assay controls. Furthermore, histones are unstable in plasma/serum, limiting their utility in liquid biopsies, which are rapidly becoming the new focus of nucleosome PTM assay and biomarker development.

Figures 2A, 2B:
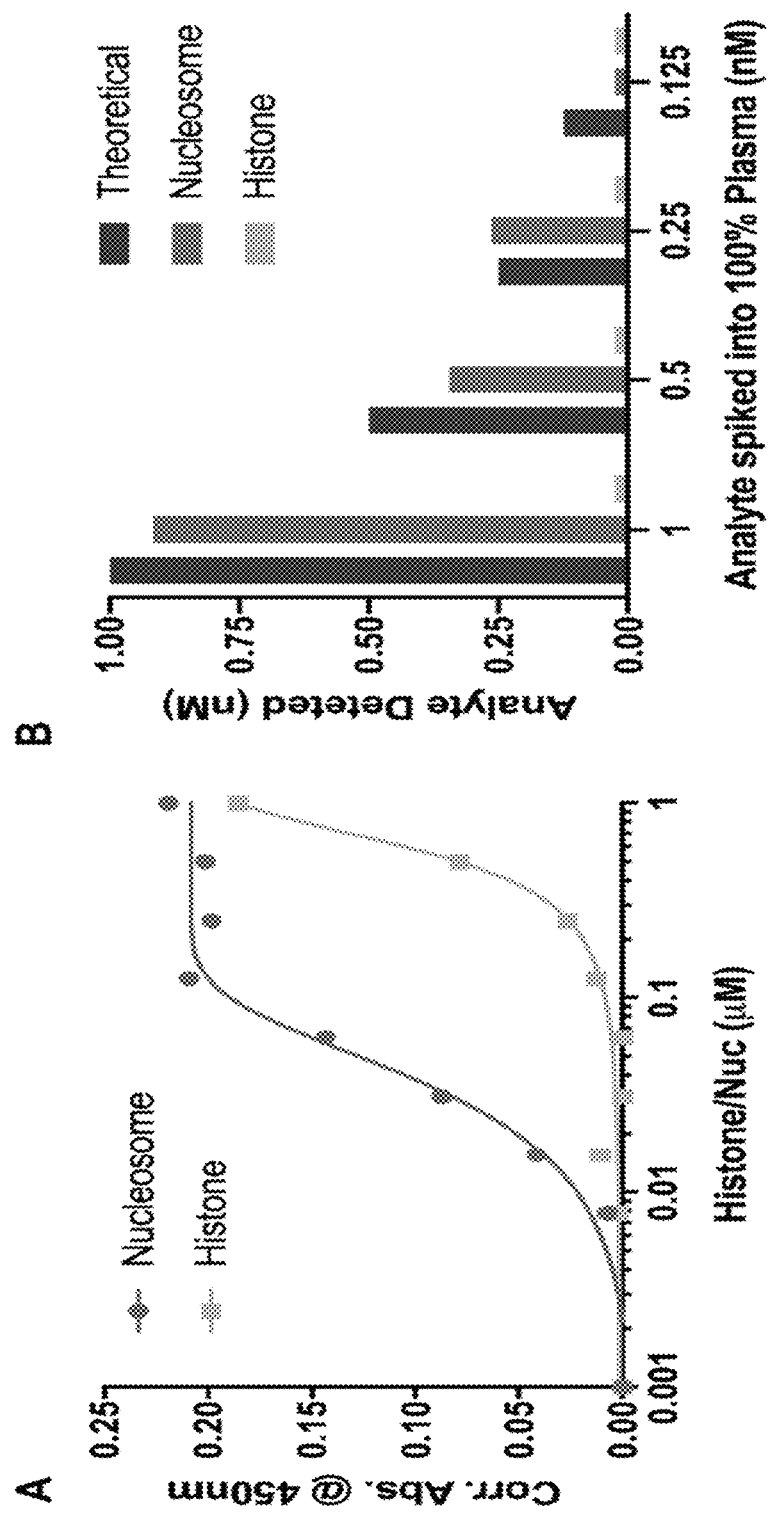
FIGS. 2A-2B show nucleosomes are recovered at expected values and provide reliable calibration in human plasma. A sandwich ELISA was developed to measure nucleosome citrullination, using H3R2cit/R8cit/R17cit histones and dNucs as substrates. Substrates were captured using an anti-H3R2cit/R8cit/R17cit antibody; detection was performed using an HRP-conjugated antibody specific for the unmodified C-terminus of H3. (A) Standard curve using citrullinated H3 or dNucs spiked in 5% human plasma. (B) Recovery of citrullinated H3 or dNuc spiked into 100% plasma. Samples were diluted 20-fold prior to ELISA and normalized to standards in (A). Theoretical=expected normalized value.

In FIGS. 2A-2B, the recovery of citrullinated dNucs and histone H3 subunits spiked into healthy human plasma was compared. For this, a standard sandwich ELISA was developed to measure histone citrullination: an anti-H3R2cit/ R8cit/R17cit antibody was used to capture substrates, followed by detection with an HRP-conjugated antibody specific to the unmodified C-terminus of H3. In FIG. 2A, H3R2cit/R8cit/R17cit histone or dNucs were spiked at a 1,000-fold range (1 nM to 1 μM) into 5% human plasma. Note that the ELISA signal is dramatically reduced when quantified in plasma with citrullinated histone H3 vs. dNucs. These results demonstrate: 1) linear recovery of citrullinated dNucs spiked into plasma; and 2) increased sensitivity of citrullinated dNuc detection in plasma compared to citrullinated H3 (i.e., wider range of analyte detection).

Reliable calibrants are stable in assay matrix (e.g., plasma or cell lysates). To determine if loss of histone signal observed is due to aberrant aggregation or interactions with plasma proteins, H3R2cit/R8cit/R17cit histone or dNuc substrates were spiked into 100% plasma then diluted samples to 5% plasma and quantified H3 citrullination (FIG. 2B). Samples were normalized to standards prepared in 5% plasma (FIG. 2A). Of note, citrullinated dNucs were readily recovered at expected values (FIG. 2B). However, citrullinated histone H3 were significantly lower (i.e., not detectable) when added to 100% plasma vs. 5%. These data demonstrate that only citrullinated dNucs (not histone H3) provide reliable calibration in plasma samples. In addition, the results support the development of dNucs as reliable standards for next-generation liquid biopsy assays, enabling accurate quantification of histone PTMs directly from patient plasma.

Example 3: Optimization of ELISA to Nucleosome PTMs Using Combinatorially Modified dNucs Since dNucs are structurally analogous and display similar binding characteristics to endogenous nucleosomes (Shah et al., *Mol. Cell* 72(1):162 (2018)), it was reasoned that they may be used to design highly sensitive and specific histone PTM detection assays. Here, the H3R2cit/R8cit/ R17cit dNuc was applied to the development of an ELISA for the detection of nucleosome citrullination. The dNucs were first used to identify highly specific antibodies with low off-target PTM binding activity. The dNucs were then applied as highly purified substrates for ELISA development, using various pairs of capture and detection antibodies. All three examples depicted in FIGS. 3A-3C used a PTM-specific (anti-H3R8cit) capture antibody paired with three different types of biotinylated detection antibodies: 1) an antibody directed to an unmodified portion of histone H3 (FIG. 3A); 2) an antibody recognizing another co-occurring PTM, H3R2cit (FIG. 3B); and 3) the same anti-H3R8cit antibody used for dNuc capture (FIG. 3C). ELISA signal was generated using a streptavidin-conjugated HRP (SA-HRP). For all three experiments shown, unmodified dNuc was included as a negative control, to monitor background signal.

Surprisingly, the assay with highest sensitivity and lowest background used the same anti-H3R8cit antibody for both capture and detection (FIG. 3C, bottom). Targeting different PTMs (FIG. 3B) had similar specificity, but exhibited slightly elevated background in the unmodified Nuc control. These experiments demonstrate the remarkable capabilities of the antibodies to bind multiple PTMs on the same nucleosome (e.g., H3R8Cit/H3R2Cit or H3R8cit/H3R8cit), which may enable the quantification of co-occurring PTMs in future studies. Of note, there are two copies of each histone subunit (e.g., H2A, H2B, H3, and H4) in a nucleosome. Thus, it remains unclear if the H3R8cit/H3R2cit ELISA combination is detecting these histone PTMs in cis or trans. The development of nucleosomes carrying modifications asymmetrically (i.e., where only one of the histone subunits are modified) will be required to determine these potential modes of action.

Detection with an anti-histone H3 antibody (FIG. 3A, bottom) displayed substantially reduced sensitivity compared to detection with PTM-antibodies. Notably, this type of capture/detection setup is the customary industry approach for ELISA of histone PTMs (using histone-based substrates or standards), suggesting that there are significant gains to be made in assay specificity and sensitivity by leveraging the nucleosome structure. Indeed, existing assays measuring nucleosome PTMs are developed using purified histone extracts or human plasma with unknown endogenous levels of target analyte. As demonstrated in FIGS. 3A-3C, the generation of highly purified dNucs allows one to empirically determine the most sensitive and specific antibody pair for ELISA, delivering assays with unparalleled accuracy and precision. Furthermore, the linear recovery of dNucs signal supports the continued development of dNucs as nucleosome PTM-specific assay calibrators.

Example 4: dNucs are Reliably Recovered and Quantified from Human Plasma

Figure 4A:
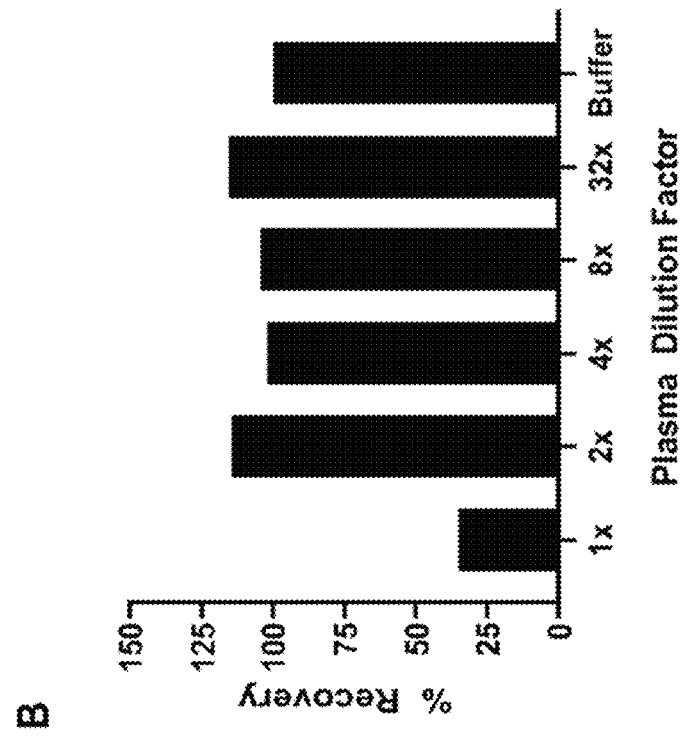
FIGS. 4A-4B show that recombinant modified dNucs are reliably recovered and quantified from human plasma. The optimized sandwich ELISA uses an anti-H3R8cit antibody for substrate capture, followed by incubation with biotinylated anti-H3R2cit antibody, and detection with streptavidin-HRP. (A) H3R2cit/R8cit/R17cit dNucs were spiked into standard ELISA buffer to generate a standard curve. (B) H3R2cit/R8cit/R17cit dNucs were spiked into varying dilutions of healthy human plasma, and the percent recovery was interpolated from the standard curve shown in (A).
Figure 4B:
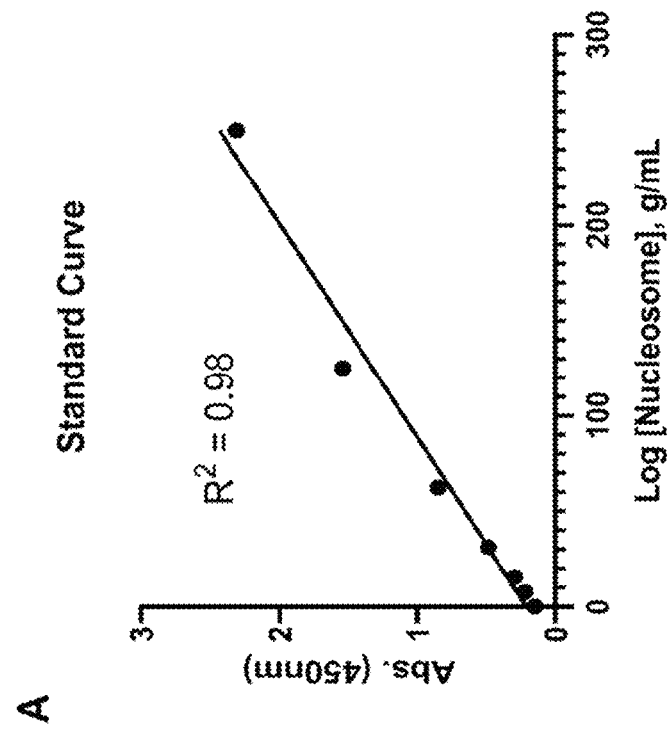

The utility of dNucs as calibrators in clinical assays relies on their ability to be accurately recovered from a biological matrix, such as plasma. Here one of the optimized sandwich ELISAs from FIGS. 3A-3C was employed, using anti-H3R8cit antibody for substrate capture, followed by detection with biotinylated anti-H3R2cit antibody and streptavidin-HRP. First, a standard curve was generated using H3R2cit/R8cit/R17cit dNucs spiked at a six-point concentration range into ELISA buffer (FIG. 4A) The standard curve demonstrates consistent linear recovery of dNucs in ELISA buffer, with an $R^2$=0.98. In parallel experiments, H3R2cit/R8cit/R17cit dNucs (50 ng/mL) were spiked into varying dilutions of healthy human plasma, and the percent recovery was interpolated from the standard curve (FIG. 4B). These results demonstrate>95% recovery of dNuc signal in plasma diluted 2×-32×, indicating minimal interference with assay matrix, and suggests that the dNucs provide highly stable and reliable quantitative standards across a wide range of plasma dilutions.

Example 5: dNucs Estimate Concentrations of Endogenous Circulating Modified Nucleosomes in Human Plasma Full application of dNucs as assay calibrators requires that they behave similarly to endogenous nucleosomes (i.e., binding and detection characteristics). Towards this aim, plasma was collected from patients with moderate and severe rheumatoid arthritis (RA) symptoms (based on DAS28 score (Prevoo et al., *Arthritis Rheum.* 38(1):44 (1995)). RA patients have high levels of nucleosome citrullination (Pratesi et al., *Ann. Rheum. Dis.* 73(7):1414 (2014); Dwivedi et al., *FASEB J.* 28(7):2840 (2014); Sohn et al., *Arthritis Rheumatol.* 67(11):2877 (2015)), making them an ideal candidate for this proof-of-concept study. Plasma from RA patients (along with age- and sex-matched healthy controls) was diluted 2× to 128× and analyzed in ELISA (FIGS. 5B, 5D). For this study, the ELISA for nucleosome citrullination detection was utilized, using anti-H3R8cit antibody for nucleosome capture and a biotinylated anti-H3R2cit antibody and streptavidin-HRP for detection. Standard curves were generated using H3R2cit/R8cit/R17cit dNucs spiked at a six-point concentration range in ELISA buffer, and were analyzed using linear (FIG. 5A) and non-linear (FIG. 5C) regression methods. Shown here (FIGS. 5B, 5D) are the averages for one patient from each category (healthy, moderate RA, and severe RA) from our ongoing study.

Figure 5A:
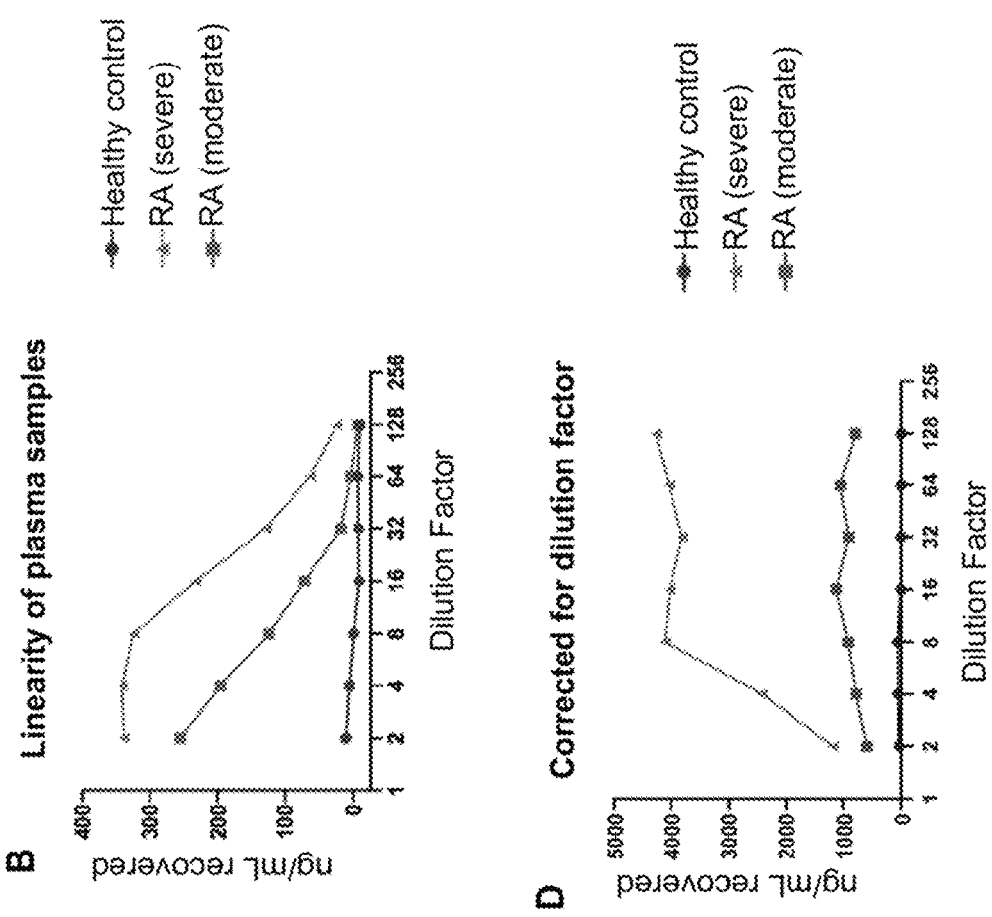
FIGS. 5A-5D show dNucs estimate concentrations of endogenous circulating modified nucleosomes in human plasma. (A, C) H3R2cit/R8cit/R17cit dNucs were used to generate standard curves for quantifying nucleosome citrullination using both linear (A) and non-linear (C) regression methods. (B, D) Plasma from patients diagnosed with severe and moderate rheumatoid arthritis (RA), a pathology associated with high levels of nucleosome citrullination in blood, and healthy controls were diluted and analyzed by ELISA. (B) Linear dilution of human plasma samples parallels the linear standard curve (A), establishing dNucs as suitable references for endogenous nucleosomes. (D) Normalization using non-linear standard curves provides accurate and consistent recovery across a wide range of plasma dilutions, and demonstrates altered levels of nucleosome citrullination between controls and moderate to severe RA. For all images in FIGS. 5A-5D, ELISA was performed using an anti-H3R8cit antibody for substrate capture, followed by incubation with biotinylated anti-H3R2cit antibody, and detection with streptavidin-HRP.
Figure 5B:
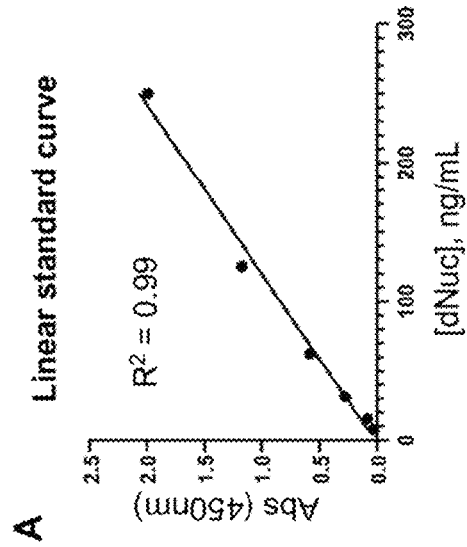
Figure 5C:
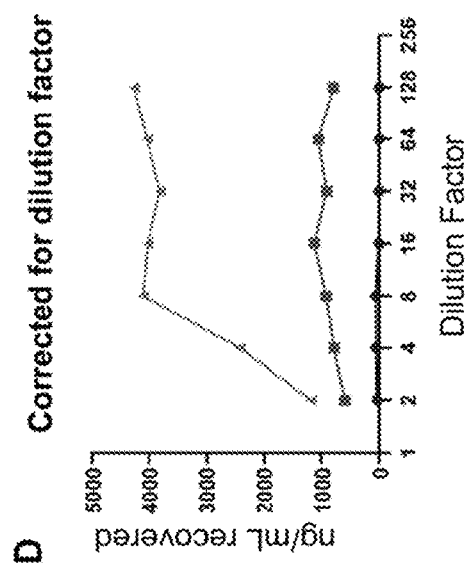
Figure 5D:
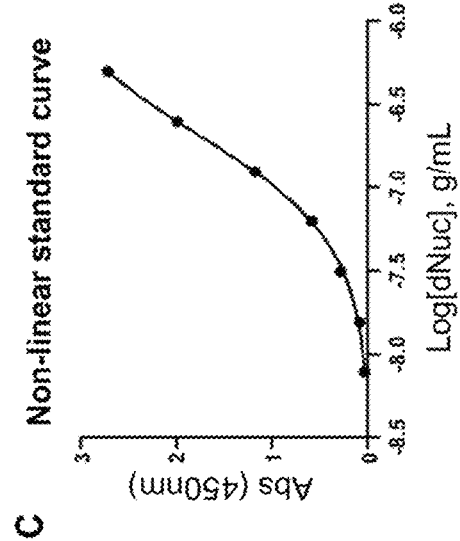

As shown in FIG. 5B, dilution of human plasma samples generated a linear curve similar to that from the standard curve in FIG. 5A. These data confirm that the standard curve accurately represented the sample-dilution curve, validating the use of chosen calibrator for quantifying endogenous material. ELISA data also was normalized using the non-linear standard curve (FIGS. 5C, 5D), which provided consistent recovery across a wide range of plasma dilutions. In addition, these analyses demonstrate altered levels of nucleosome citrullination between controls and moderate to severe RA, supporting the implementation of dNucs as standards for quantification in clinically-relevant assays.

The foregoing is illustrative of the present invention, and is not to be construed as limiting thereof. The invention is defined by the following claims, with equivalents of the claims to be included therein.

TABLE 1(a)

Post translational modifications for Human Histones H2A type 1/2/3, H2A.X, H2A.Z and H2A.V Isoform 1/2/3/4/5

| Position | Description of Modification Type |
|---|---|
| Human Histone H2a type 1/2/3 | |
| 1 | N-acetylserine |
| 1 | Phosphoserine |
| 3 | Citrulline |
| 5 | N6-acetyllysine |
| 36 | N6-crotonyl-L-lysine |
| 118 | N6-crotonyl-L-lysine |
| 119 | N6-crotonyl-L-lysine |
| 120 | Phosphothreonine |
| 126 | N6-crotonyl-L-lysine |
| 13 | Glycyl lysine isopeptide (Lys-Gly) (interchain with G-Cter in ubiquitin) |
| 15 | Glycyl lysine isopeptide (Lys-Gly) (interchain with G-Cter in ubiquitin) |
| 119 | Glycyl lysine isopeptide (Lys-Gly) (interchain with G-Cter in ubiquitin) |
| Human Histone H2A.X | |
| 1 | N-acetylserine |
| 1 | Phosphoserine |
| 36 | N6-acetyllysine |
| 119 | Phosphoserine |
| 142 | Phosphotyrosine |
| 13 | Glycyl lysine isopeptide (Lys-Gly) (interchain with G-Cter in ubiquitin) |

TABLE 1(a)-continued

Post translational modifications for Human Histones H2A type 1/2/3, H2A.X, H2A.Z and H2A.V Isoform 1/2/3/4/5

| Position | Description of Modification Type |
|---|---|
| 15 | Glycyl lysine isopeptide (Lys-Gly) (interchain with G-Cter in ubiquitin) |
| 119 | Glycyl lysine isopeptide (Lys-Gly) (interchain with G-Cter in ubiquitin) |
| Human Histone H2A.Z | |
| 1 | N-acetylalanine |
| 4 | N6-acetyllysine |
| 7 | N6-acetyllysine |
| 11 | N6-acetyllysine |
| 13 | N6-acetyllysine |
| 121 | Glycyl lysine isopeptide (Lys-Gly) (interchain with G-Cter in ubiquitin) |
| Human Histone H2A.V Isoform 1/2/3/4/5 | |
| 4 | N6-acetyllysine |
| 7 | N6-acetyllysine |
| 11 | N6-acetyllysine |
| 121 | Glycyl lysine isopeptide (Lys-Gly) (interchain with G-Cter in ubiquitin) |

TABLE 1(b)

Post translational modifications for Human Histone H2A.J and H2B type 1

| Position | Description of Modification Type |
|---|---|
| Human Histone H2A.J | |
| 1 | N-acetylserine |
| 1 | Phosphoserine |
| 5 | N6-acetyllysine |
| 120 | Phosphothreonine |
| 122 | Phosphoserine |
| 13 | Glycyl lysine isopeptide (Lys-Gly) (interchain with G-Cter in ubiquitin) |
| 15 | Glycyl lysine isopeptide (Lys-Gly) (interchain with G-Cter in ubiquitin) |
| 119 | Glycyl lysine isopeptide (Lys-Gly) (interchain with G-Cter in ubiquitin) |
| Human Histone H2B type 1 | |
| 1 | N-acetylproline |
| 6 | N6-acetyllysine |
| 6 | N6-crotonyl-L-lysine |
| 12 | N6-acetyllysine |
| 12 | N6-crotonyl-L-lysine |
| 13 | N6-acetyllysine |
| 13 | N6-crotonyl-L-lysine |
| 16 | N6-acetyllysine |
| 16 | N6-crotonyl-L-lysine |
| 17 | N6-acetyllysine |
| 17 | N6-crotonyl-L-lysine |
| 21 | N6-acetyllysine |
| 21 | N6-crotonyl-L-lysine |
| 24 | N6-acetyllysine |
| 24 | N6-crotonyl-L-lysine |
| 35 | N6-crotonyl-L-lysine |
| 37 | Phosphoserine |
| 47 | N6-methyllysine |
| 58 | N6,N6-dimethyllysine |
| 80 | Dimethylated arginine |
| 85 | Phosphoserine |
| 86 | N6,N6,N6-trimethyllysine |
| 86 | N6-acetyllysine |
| 87 | Omega-N-methylarginine |
| 93 | Omega-N-methylarginine |
| 109 | N6-methyllysine |
| 116 | Phosphothreonine |

TABLE 1(b)-continued

Post translational modifications for
Human Histone H2A.J and H2B type 1

| Position | Description of Modification Type |
|---|---|
| 117 | N6-methylated lysine |
| 35 | Glycyl lysine isopeptide (Lys-Gly) (interchain with G-Cter in ubiquitin) |
| 121 | Glycyl lysine isopeptide (Lys-Gly) (interchain with G-Cter in ubiquitin) |

TABLE 1(c)

Post translational modifications for
Human Histone H2B type 2/3/F-S

| Position | Description of Modification Type |
|---|---|
| 1 | N-acetylproline |
| 5 | N6-acetyllysine |
| 5 | N6-crotonyl-L-lysine |
| 11 | N6-acetyllysine |
| 11 | N6-crotonyl-L-lysine |
| 12 | N6-acetyllysine |
| 12 | N6-crotonyl-L-lysine |
| 14 | Phosphoserine |
| 15 | N6-acetyllysine |
| 15 | N6-crotonyl-L-lysine |
| 16 | N6-acetyllysine |
| 16 | N6-crotonyl-L-lysine |
| 20 | N6-acetyllysine |
| 20 | N6-crotonyl-L-lysine |
| 23 | N6-acetyllysine |
| 23 | N6-crotonyl-L-lysine |
| 34 | N6-crotonyl-L-lysine |
| 36 | Phosphoserine |
| 46 | N6-methyllysine |
| 57 | N6,N6-dimethyllysine |
| 79 | Dimethylated arginine |
| 85 | N6,N6,N6-trimethyllysine |
| 85 | N6-acetyllysine |
| 86 | Omega-N-methylarginine |
| 92 | Omega-N-methylarginine |
| 108 | N6-methyllysine |
| 115 | Phosphothreonine |
| 116 | N6-methylated lysine |
| 112 | O-linked (GlcNAc) |
| 34 | Glycyl lysine isopeptide (Lys-Gly) (interchain with G-Cter in ubiquitin) |
| 121 | Glycyl lysine isopeptide (Lys-Gly) (interchain with G-Cter in ubiquitin) |

TABLE 1(d)

Post translational modifications for Human
Putative Histone H2B type 2-D/2-C

| Position | Description of Modification Type |
|---|---|
| 1 | N-acetylproline |
| 5 | N6-acetyllysine |
| 5 | N6-crotonyl-L-lysine |
| 11 | N6-acetyllysine |
| 11 | N6-crotonyl-L-lysine |
| 12 | N6-acetyllysine |
| 12 | N6-crotonyl-L-lysine |
| 14 | Phosphoserine |
| 15 | N6-acetyllysine |
| 15 | N6-crotonyl-L-lysine |
| 16 | N6-acetyllysine |
| 16 | N6-crotonyl-L-lysine |
| 20 | N6-acetyllysine |
| 20 | N6-crotonyl-L-lysine |
| 23 | N6-acetyllysine |
| 23 | N6-crotonyl-L-lysine |
| 34 | N6-crotonyl-L-lysine |
| 36 | Phosphoserine |
| 46 | N6-methyllysine |
| 57 | N6,N6-dimethyllysine |
| 79 | Dimethylated arginine |
| 85 | N6,N6,N6-trimethyllysine |
| 85 | N6-acetyllysine |
| 86 | Omega-N-methylarginine |
| 92 | Omega-N-methylarginine |

TABLE 1(e)

Post translational modifications for Human
Histone H3.1/H3.1t/H3.2/H3.3/H3.3C

| Position | Modification Type |
|---|---|
| 2 | Asymmetric dimethylarginine |
| 3 | Phosphothreonine |
| 4 | Allysine |
| 4 | N6,N6,N6-trimethyllysine |
| 4 | N6,N6-dimethyllysine |
| 4 | N6-acetyllysine |
| 4 | N6-crotonyl-L-lysine |
| 4 | N6-methyllysine |
| 6 | Phosphothreonine |
| 8 | Citrulline |
| 8 | Symmetric dimethylarginine |
| 9 | N6,N6,N6-trimethyllysine |
| 9 | N6,N6-dimethyllysine |
| 9 | N6-acetyllysine |
| 9 | N6-crotonyl-L-lysine |
| 9 | N6-methyllysine |
| 10 | Phosphoserine |
| 11 | Phosphothreonine |
| 14 | N6-acetyllysine |
| 17 | Asymmetric dimethylarginine |
| 17 | Citrulline |
| 18 | N6-acetyllysine |
| 18 | N6-crotonyl-L-lysine |
| 18 | N6-methyllysine |
| 23 | N6-acetyllysine |
| 23 | N6-crotonyl-L-lysine |
| 23 | N6-methyllysine |
| 27 | N6,N6,N6-trimethyllysine |
| 27 | N6,N6-dimethyllysine |
| 27 | N6-acetyllysine |
| 27 | N6-crotonyl-L-lysine |
| 27 | N6-methyllysine |
| 28 | Phosphoserine |
| 36 | N6,N6,N6-trimethyllysine |
| 36 | N6,N6-dimethyllysine |
| 36 | N6-acetyllysine |
| 36 | N6-methyllysine |
| 37 | N6-methyllysine |
| 41 | Phosphotyrosine |
| 56 | N6,N6,N6-trimethyllysine |
| 56 | N6-acetyllysine |
| 56 | N6-crotonyl-L-lysine |
| 56 | N6-methyllysine |
| 57 | Phosphoserine |
| 64 | N6-methyllysine |
| 79 | N6,N6,N6-trimethyllysine |
| 79 | N6,N6-dimethyllysine |
| 79 | N6-acetyllysine |
| 79 | N6-methyllysine |
| 80 | Phosphothreonine |
| 107 | Phosphothreonine |
| 115 | N6-acetyllysine |
| 122 | N6-acetyllysine |
| 122 | N6-methyllysine |

TABLE 1(f)

Post translational modifications for Human Histone
H3-like centromeric protein A and Human Histone H4

| Position | Description of Modification Type |
|---|---|
| *Human Histone H3-like centromeric protein A* | |
| 6 | Phosphoserine; by AURKA and AURKB |
| 16 | Phosphoserine |
| 18 | Phosphoserine |
| 26 | Phosphoserine |
| *Human Histone H4* | |
| 1 | N-acetylserine |
| 1 | Phosphoserine |
| 3 | Asymmetric dimethylarginine |
| 3 | Citrulline |
| 3 | Omega-N-methylarginine |
| 3 | Symmetric dimethylarginine |
| 5 | N6-acetyllysine |
| 5 | N6-crotonyl-L-lysine |
| 8 | N6-acetyllysine |
| 8 | N6-crotonyl-L-lysine |
| 12 | N6-acetyllysine |
| 12 | N6-crotonyl-L-lysine |
| 16 | N6-acetyllysine |
| 16 | N6-crotonyl-L-lysine |
| 20 | N6,N6,N6-trimethyllysine |
| 20 | N6,N6-dimethyllysine |
| 20 | N6-methyllysine |
| 31 | N6-acetyllysine |
| 47 | Phosphoserine |
| 51 | Phosphotyrosine |
| 88 | Phosphotyrosine |
| 91 | N6-acetyllysine |
| 91 | Glycyl lysine isopeptide (Lys-Gly) (interchain with G-Cter in ubiquitin) |

We claim:

1. A method for quantifying the abundance of a histone or DNA modification on an intact nucleosome in a biological sample from a subject, the method comprising:
   a. isolating a biological sample comprising nucleosomes comprising one or more core histone and/or DNA modifications in a target epitope;
   b. preparing the biological sample for an immunoassay that measures total levels of modified histone or DNA;
   c. providing a recombinant mono- and/or polynucleosome sample comprising a core histone modification and/or DNA modification target epitope at various concentrations to create a series of reference standard samples separate from the biological sample for generating a standard curve;
   d. adding an affinity reagent to the biological sample and recombinant nucleosome reference samples;
   e. performing an affinity reagent-based assay to measure the relative amount of modified histone or DNA levels in the biological sample and the recombinant nucleosome reference standard samples; and
   f. quantifying the abundance of histone modification or DNA modification in the target epitope by comparing the relative abundance in the biological sample to the reference standard.

2. A method for quantifying the abundance of two or more histone or DNA modifications on an intact single nucleosome in a biological sample from a subject, the method comprising:
   a. isolating a biological sample comprising nucleosomes comprising two or more core histone and/or DNA modifications in target epitopes;
   b. preparing the biological sample for an immunoassay that measures total levels of modified histone or DNA;
   c. providing a recombinant mono- and/or polynucleosome sample comprising a core histone modification and/or DNA modification target epitope at various concentrations to create a series of reference standard samples separate from the biological sample for generating a standard curve;
   d. adding two or more affinity reagents to the biological sample and recombinant nucleosome reference samples;
   e. performing an affinity reagent-based assay to measure the relative amount of modified histone or DNA levels in the biological sample and recombinant nucleosome reference standard samples; and
   f. quantifying the abundance of histone modification or DNA modification in the target epitopes by comparing the relative abundance in the biological sample to the reference standard.

3. The method of claim 1, wherein the biological sample is treated with an enzyme to digest chromatin into mono- and/or polynucleosomes.

4. The method of claim 3, wherein the enzyme is micrococcal nuclease.

5. The method of claim 1, wherein the biological sample comprises cells and the chromatin is isolated from the cells.

6. The method of claim 5, where in the cells are cells from a disease or disorder associated with epigenetic modifications.

7. The method of claim 5, wherein the cells are not cells from a disease or disorder associated with epigenetic modifications.

8. The method of claim 1, wherein the biological sample is a biopsy.

9. The method of claim 1, wherein the biological sample is a biological fluid.

10. The method of claim 1, wherein the biological sample comprises peripheral blood mononuclear cells.

11. The method of claim 1, wherein the biological sample comprises circulating nucleosomes.

12. The method of claim 11, wherein the circulating nucleosomes are from blood.

13. The method of claim 12, wherein the circulating nucleosomes are from cells from a disease or disorder associated with epigenetic modifications.

14. The method of claim 11, wherein the biological sample is plasma, urine, saliva, stool, lymphatic fluid, or cerebrospinal fluid.

15. The method of claim 1, wherein the subject is a human.

16. The method of claim 1, wherein the affinity agent is an antibody or a fragment thereof directed towards the epitope.

17. The method of claim 1, wherein at least one or more nucleosome modification(s) on the same nucleosome are quantified.

18. The method of claim 1, wherein at least one or more nucleosome modification(s) on different nucleosomes are quantified.

19. The method of claim 1, wherein quantification of at least one or more nucleosome modification(s) is determined by an antibody-based detection assay.

20. The method of claim 19, wherein the antibody-based detection method is selected from the group consisting of ELISA, AlphaLISA, AlphaSCREEN, Luminex, and immunoblotting.

21. The method of claim 19, wherein the antibody-based detection assay uses two different antibodies for substrate capture and detection.

22. The method of claim 21, wherein the capture and detection antibodies specifically bind a histone post-translational modification (PTM) and another nucleosome structure.

23. The method of claim 21, wherein the capture and detection antibodies specifically bind two different histone PTMs.

24. The method of claim 19, wherein the antibody-based detection assay uses the same antibody for both substrate capture and detection.

25. The method of claim 1, wherein the nucleosome comprises at least one post-translational amino acid modification or DNA modification selected from the group consisting of N-acetylation of serine and alanine; phosphorylation of serine, threonine and tyrosine; N-crotonylation, N-acylation of lysine; N6-methylation, N6,N6-dimethylation, N6,N6,N6-trimethylation of lysine; omega-N-methylation, symmetrical-dimethylation, asymmetrical-dimethylation of arginine; citrullination of arginine; ubiquitinylation of lysine; sumoylation of lysine; O-methylation of serine and threonine, ADP-ribosylation of arginine, aspartic acid and glutamic acid; oncogenic K-to-M mutations; 5-methylcytosine, 5-hydroxymethylcytosine, 5-formylcytosine, 5-carboxylcytosine, 3-methylcytosine, 5,6-dihydrouracil, 7-methylguanosine, xanthosine, and inosine.

26. The method of claim 6, wherein the disease or disorder associated with epigenetic modifications is selected from the group consisting of renal cell carcinoma, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullar carcinoma, mastocytoma, mesothelioma, synovioma, melanoma, leiomyosarcoma, rhabdomyosarcoma, neuroblastoma, retinoblastoma, glioblastoma, oligodendroglioma, acoustic neuroma, hemangioblastoma, meningioma, pinealoma, ependymoma, craniopharyngioma, epithelial carcinoma, embryonic carcinoma, squamous cell carcinoma, base cell carcinoma, fibrosarcoma, myxoma, myxosarcoma, glioma, liposarcoma, infections caused by *Helicobacter pylori, Listeria monocytogenes, Shigella flexneri, Anaplasma phagocytophilum, Chlamydophila*, Epstein-Barr Virus, herpes, HIV, *Schistosoma haematobium*; Obesity, diabetes, heart disease; autism, fragile X syndrome, ATR-X syndrome, Angelman syndrome, Prader-Willi syndrome, Beckwith Wiedemann syndrome, Rett syndrome, Rubinstein-Taybi syndrome, Coffin-Lowry syndrome Immunodeficiency-centrometric instability-facial anomalies syndrome, α-thalassaemia, leukemia, Huntington's disease, schizophrenia, bipolar disease, aging, dementia, Alzheimer's disease, Parkinson's disease, Cornelia de Langue syndrome, Kabuki syndrome, Sjogren's syndrome, Vitiligo, progressive systemic sclerosis, psoriasis, primary biliary cirrhosis, Crohn's disease and ulcerative colitis, Hashimoto's thyroiditis, Grave's disease, inflammatory bowel disease, atherosclerosis, and cardiac hypertrophy.

27. The method of claim 1, wherein modified recombinant nucleosomes are used as controls to confirm combinatorial modifications are detected on a single or adjacent nucleosomes.

\* \* \* \* \*

UNITED STATES PATENT AND TRADEMARK OFFICE
CERTIFICATE OF CORRECTION

PATENT NO. : 10,787,697 B2
APPLICATION NO. : 16/678686
DATED : September 29, 2020
INVENTOR(S) : Cowles et al.

Page 1 of 1

It is certified that error appears in the above-identified patent and that said Letters Patent is hereby corrected as shown below:

In the Claims

Column 29, Line 50, Claim 1: Please correct "nucleosome reference samples;" to read -- nucleosome reference sample, wherein the affinity reagent targets modified histone or modified DNA; --

Column 29, Line 51, Claim 1: Please correct "performing an affinity reagent-based assay" to read -- performing an immunoassay using the affinity reagent --

Column 30, Line 9, Claim 2: Please correct "nucleosome reference samples;" to read -- nucleosome reference sample, wherein the affinity reagent targets modified histone or modified DNA; --

Column 30, Line 10, Claim 2: Please correct "performing an affinity reagent-based assay" to read -- performing an immunoassay using the affinity reagent --

Signed and Sealed this
Eleventh Day of May, 2021

Drew Hirshfeld
*Performing the Functions and Duties of the
Under Secretary of Commerce for Intellectual Property and
Director of the United States Patent and Trademark Office*